United States Patent
Kaneko et al.

(10) Patent No.: US 11,408,817 B2
(45) Date of Patent: Aug. 9, 2022

(54) DETECTION CHIP, DETECTION SYSTEM, AND DETECTION METHOD

(71) Applicant: Otsuka Pharmaceutical Co., Ltd., Tokyo (JP)

(72) Inventors: Tomonori Kaneko, Hachioji (JP); Kosuke Nagae, Tokyo (JP); Takatoshi Kaya, Inagi (JP); Yukito Nakamura, Hachioji (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 766 days.

(21) Appl. No.: 16/319,046

(22) PCT Filed: Jul. 24, 2017

(86) PCT No.: PCT/JP2017/026684
§ 371 (c)(1),
(2) Date: Jan. 18, 2019

(87) PCT Pub. No.: WO2018/021238
PCT Pub. Date: Feb. 1, 2018

(65) Prior Publication Data
US 2021/0356386 A1 Nov. 18, 2021

(30) Foreign Application Priority Data
Jul. 28, 2016 (JP) .............................. JP2016-148345

(51) Int. Cl.
*G01N 21/03* (2006.01)
*G01N 21/64* (2006.01)
(Continued)

(52) U.S. Cl.
CPC ....... *G01N 21/0303* (2013.01); *G01N 21/648* (2013.01); *G01N 21/6486* (2013.01);
(Continued)

(58) Field of Classification Search
CPC ............ G01N 21/0303; G01N 21/648; G01N 21/6486; G01N 33/68; G01N 2021/5903; G01N 2021/6482
See application file for complete search history.

(56) References Cited

U.S. PATENT DOCUMENTS 4,833,087 A * 5/1989 Hinckley .............. B01L 3/5023
422/430
6,843,963 B1 1/2005 Jennissen et al.
(Continued)

FOREIGN PATENT DOCUMENTS

JP 2002516993 A 6/2002
JP 2004163185 A * 6/2004 ............. G01N 21/27
(Continued)

OTHER PUBLICATIONS

Ogawa et al.—JP-2007047004-A—Google Patents English obtained Oct. 14, 2021 (Year: 2021).*
(Continued)

*Primary Examiner* — David P Porta
*Assistant Examiner* — Jeremy S Valentiner
(74) *Attorney, Agent, or Firm* — Lucas & Mercanti, LLP

(57) ABSTRACT

The detection system according to the present invention has a detection chip, a light source, and a detection unit. The detection chip has a housing that has an opening at an upper portion, and a reaction field for trapping a substance to be detected, the reaction field being arranged on an inner surface of the side walls included in the housing. The light source irradiates the detection chip with light from the outside such that evanescent light or surface plasmon resonance is generated under the reaction field. The detection unit detects light which is emitted from the detection chip when the light source irradiates the detection chip with light,
(Continued)

and the amount of which changes depending on the amount of the substance to be detected trapped in the reaction field.

20 Claims, 19 Drawing Sheets

(51) Int. Cl.
    *G01N 33/68*         (2006.01)
    *G01N 21/59*         (2006.01)

(52) U.S. Cl.
    CPC ..... *G01N 33/68* (2013.01); *G01N 2021/5903* (2013.01); *G01N 2021/6482* (2013.01)

(56) References Cited

U.S. PATENT DOCUMENTS

| | | |
|---|---|---|
| 2003/0049693 A1 | 3/2003 | Goh et al. |
| 2008/0131939 A1 | 6/2008 | Roper |
| 2013/0242298 A1* | 9/2013 | Miyaura .............. G01N 21/553 356/246 |
| 2014/0061506 A1* | 3/2014 | Kaya .................... G01N 21/648 250/459.1 |
| 2016/0355869 A1* | 12/2016 | Blair ...................... G02B 5/008 |
| 2017/0122965 A1* | 5/2017 | Murayama ............. G01N 21/51 |

FOREIGN PATENT DOCUMENTS

| | | | |
|---|---|---|---|
| JP | 2006-090758 A | 4/2006 | |
| JP | 2007047004 A * | 2/2007 | ............ G01N 21/03 |
| JP | 2007047004 A | 2/2007 | |
| JP | 2013148518 A | 8/2013 | |
| JP | 2015111063 A | 6/2015 | |
| WO | 2012/157403 A1 | 11/2012 | |
| WO | 2015/068813 A1 | 5/2015 | |
| WO | WO-2016031412 A1 * | 3/2016 | ......... G01N 33/6887 |
| WO | 2016093037 A1 | 6/2016 | |

OTHER PUBLICATIONS

Kato et al.—JP-2004163185-A—Google Patents English obtained Oct. 13, 2021 (Year: 2021).*
International Search Report dated Oct. 17, 2017 from the International Application No. PCT/JP2017/026684 and English translation.
EPO, Extended European Search Report for the corresponding European patent application No. 17834244.0, dated Sep. 30, 2019 (16 pages).
JPO, Office Action for the corresponding Japanese patent application No. 2018-529875, dated May 11, 2021, with English translation.
EPO, Office Action for the corresponding European patent application No. 17834244.0, dated May 27, 2022.

* cited by examiner

DETECTION CHIP, DETECTION SYSTEM, AND DETECTION METHOD

CROSS REFERENCE TO RELATED APPLICATION

This Application is a 371 of PCT/JP2017/026684 filed on July. 24, 2017 which, in turn, claimed the priority of Japanese Patent Application No. 2016-148345 filed on Jul. 28, 2016, both applications are incorporated herein by reference.

TECHNICAL FIELD

The present invention relates to a detection chip, a detection system, and a detection method for detecting a substance to be detected.

BACKGROUND ART

Biochemical reactions such as antigen-antibody reactions are used in biochemical examinations. For example, in a fluorescence immunoassay (hereinafter also referred to as "FIA"), a substance to be detected (antigen) is caused to react with a labeling substance containing a fluorescent substance. Thereafter, the substance to be detected labeled with the fluorescent substance is irradiated with excitation light, and the fluorescence emitted by the fluorescent substance is detected. Then, from the intensity of the detected fluorescence and the like, the amount of the substance to be detected is specified. Among such FIAs, the surface plasmon-field enhanced fluorescence spectroscopy (hereinafter also referred to as "SPFS") is known as a method capable of detecting a substance to be detected with high sensitivity in particular (see, for example, Patent Literature 1).

In the SPFS, a first trapping body (for example, a primary antibody) capable of specifically binding to a substance to be detected is immobilized on a metal film to form a reaction field for trapping the substance to be detected. For example, the reaction field is arranged on the bottom surface of a well (a bottomed recess for containing liquid). In the detection system disclosed in Patent Literature 1, a well is formed by fixing a well member having a through hole on a metal film formed on a dielectric member having a light transmitting property, and a reaction field is arranged on a metal film forming the bottom surface of the well. Then, liquid (an analyte) containing a substance to be detected is introduced into the well, thereby binding the substance to be detected to a first trapping body. Then, a second trapping body (for example, a secondary antibody) labeled with a fluorescent substance is introduced into the well, so that the second trapping body is further bound to the substance to be detected that has been bound to the first trapping body. That is, the substance to be detected is indirectly labeled with the fluorescent substance. In this state, when the metal film is irradiated with excitation light from the side of the dielectric member, the fluorescent substance is excited by an electric field enhanced by surface plasmon resonance (hereinafter also referred to as "SPR") and emits fluorescence. Then, the substance to be detected can be detected by detecting the fluorescence emitted by the fluorescent substance. In the detection system disclosed in Patent Literature 1, a detection unit for detecting fluorescence is arranged above the well, and detects fluorescence that has passed through the liquid surface of the liquid in the well.

CITATION LIST

Patent Literature

Patent Literature 1: International Publication No. 2012/157403

SUMMARY OF INVENTION

Technical Problem

In the detection system disclosed in Patent Literature 1, since the metal film and the reaction field are arranged on the bottom surface of the well, when the liquid in the well is removed, a tip of a liquid transfer device contacts the metal film or the reaction field, and there is a concern of these being damaged For this reason, the tip of the liquid transfer device cannot be pressed against the bottom surface of the well, and it is difficult to sufficiently remove the liquid in the well. If the liquid remains in the well as described above, various reactions do not proceed appropriately, and there is a concern that the detection accuracy is lowered.

In the detection system disclosed in Patent Literature 1, a detection unit is arranged above the well, and detects the fluorescence that has passed through the liquid surface of the liquid in the well. Therefore, if the inner diameter of the well is small, there is a concern that the detection result of the fluorescence is affected by the meniscus. Even when the inner diameter of the well is large, the detection result of the fluorescence may be affected by bubbles existing on the liquid surface.

An object of the present invention is to provide a detection chip, a detection system, and a detection method for detecting a substance to be detected, that can prevent deterioration of detection accuracy due to remaining liquid in a housing (well) during a reaction process, and can reduce influence on a detection result by a liquid surface of the liquid in the housing during a detection process.

SOLUTION TO PROBLEM

A detection chip according to an embodiment of the present invention includes: a well body including a housing having an opening at an upper portion and a side portion; and a side wall member on which a trapping region for trapping a substance to be detected is arranged, at least a part of the trapping region of the side wall member is exposed through the opening in the side portion of the housing into the housing, and the side wall member is fixed to the well body so as to cover at least a part of the opening in the side portion of the housing.

A detection system according to an embodiment of the present invention includes: a detection chip including a housing having an opening at an upper portion, and a reaction field for trapping a substance to be detected, the reaction field being arranged on an inner surface of a side wall included in the housing not via a metal film or via a metal film; a light source that irradiates the detection chip with light from the outside such that evanescent light is generated on the inner surface of the side wall at a position corresponding to the reaction field or surface plasmon resonance is generated in the metal film; and a detection unit that, when the light source irradiates the detection chip with light, detects light that is emitted from the detection chip and the light amount of which changes depending on the amount of the substance to be detected that has been trapped in the reaction field.

A detection method according to an embodiment of the present invention includes: a first step of causing a substance to be detected to be trapped in a reaction field of a detection chip including a housing having an opening at an upper portion, and a reaction field arranged on an inner surface of a side wall included in the housing not via a metal film or via a metal film; and a second step of irradiating the detection chip with light from the outside such that evanescent light is generated on the inner surface of the side wall at a position corresponding to the reaction field or surface plasmon resonance is generated in the metal film, and detecting light that is emitted from the detection chip and the light amount of which changes depending on the amount of the substance to be detected that has been trapped in the reaction field.

Advantageous Effects of Invention

According to the present invention, it is possible to provide a detection chip, a detection system, and a detection method for detecting a substance to be detected, that can prevent deterioration of detection accuracy due to remaining liquid in a housing during a reaction process, and can reduce influence on a detection result by a liquid surface of the liquid in the housing during a detection process.

DESCRIPTION OF EMBODIMENTS

Embodiments of the present invention will be described below with reference to the drawings. In the following description, as an embodiment of a detection chip, a detection system, and a detection method according to the present invention, a detection chip, a detection system, and a detection method for detecting a substance to be detected by the SPFS will be described. However, the detection chip, the detection system, and the detection method according to the present invention are not limited thereto.

First Embodiment

In a first embodiment, a detection chip, a detection system, and a detection method for detecting a substance to be detected by prism coupling type SPFS (PC-SPFS) that generates SPR using a prism will be described.

Figure 1:
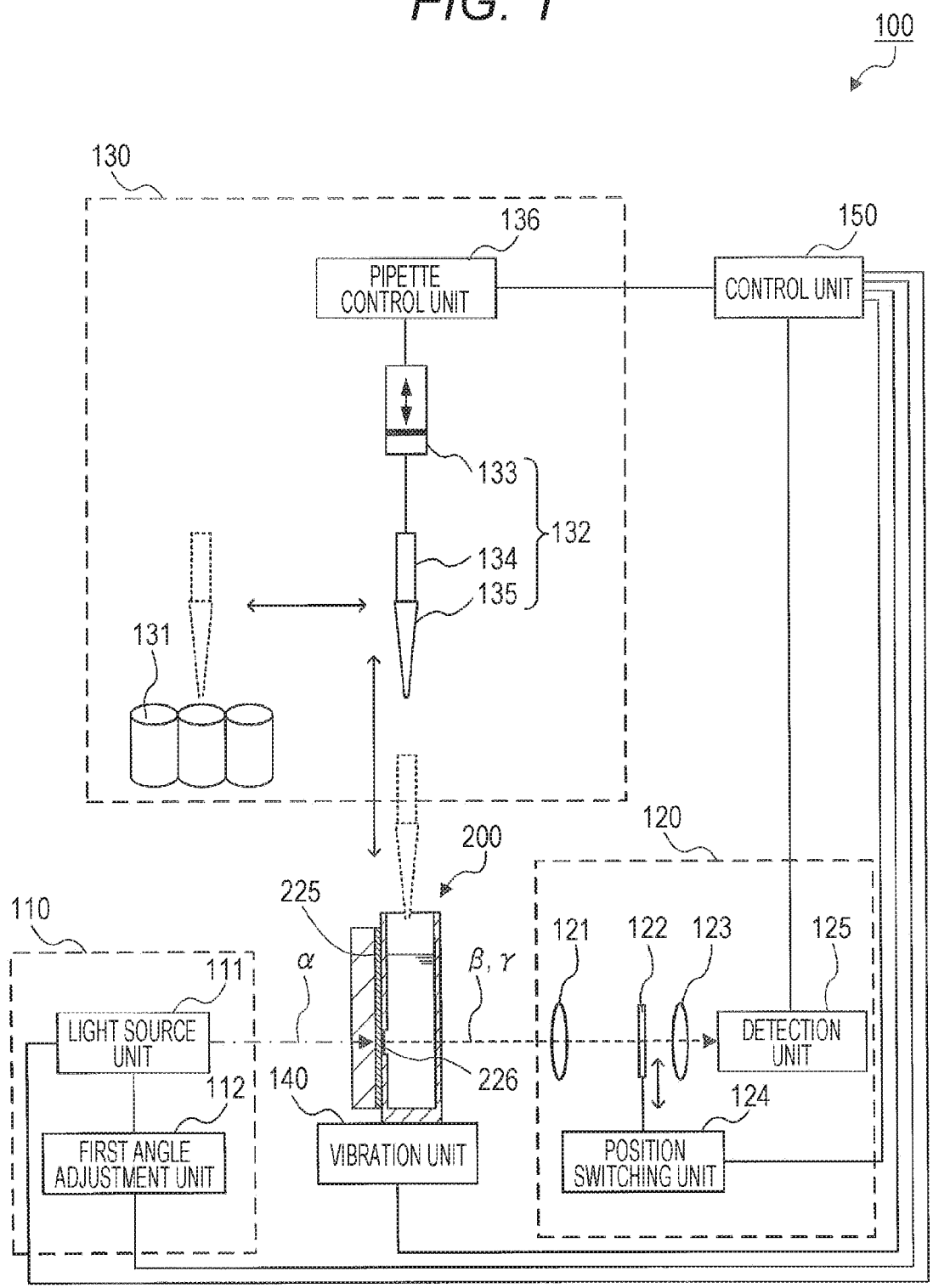
FIG. 1 is a schematic diagram showing a configuration of a detection system according to a first embodiment.

FIG. 1 is a schematic diagram showing a configuration of a detection system 100 according to the first embodiment. As shown in FIG. 1, the detection system 100 operates in a state where a detection chip 200 is mounted at a predetermined position. In addition to the detection chip 200, the detection system 100 includes an excitation light irradiation unit 110, a fluorescence detection unit 120, a liquid transfer unit 130, a vibration unit 140, and a control unit 150. In the detection system 100, the detection chip 200 is irradiated with excitation light α such that surface plasmon resonance is generated in the metal film 225 of the detection chip 200 in a state where the detection chip 200 is mounted to a predetermined position, and an enhancement electric field based on the surface plasmon resonance is generated in the vicinity of the metal film 225. Then, a fluorescent substance existing in a reaction field 226 on the metal film 225 is excited by the enhancement electric field, and fluorescence β emitted from the fluorescent substance is detected, so that the presence or absence and amount of a substance to be detected in the analyte are measured.

Hereinafter, the detection chip 200 will be described first, and then the detection system 100 and its operation (detection method) will be described.

(Detection Chip)

Figure 2C:
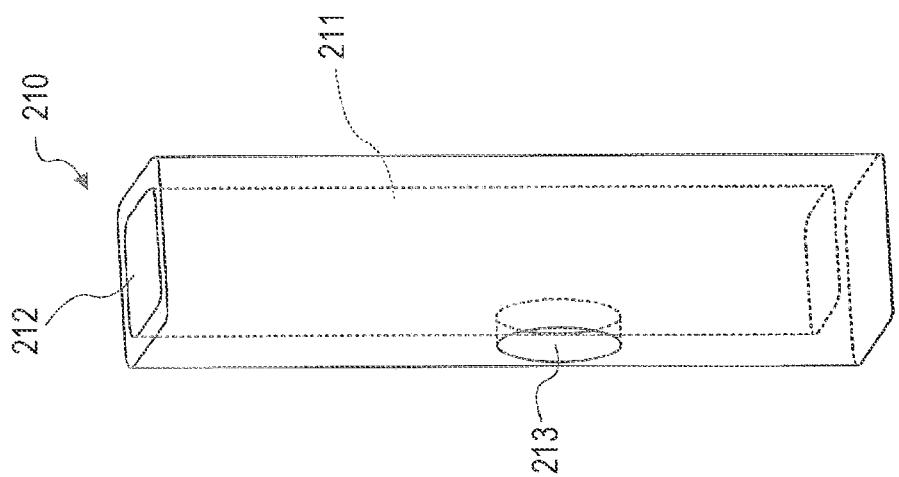
FIG. 2C is a perspective view of the well body.
Figure 2B:
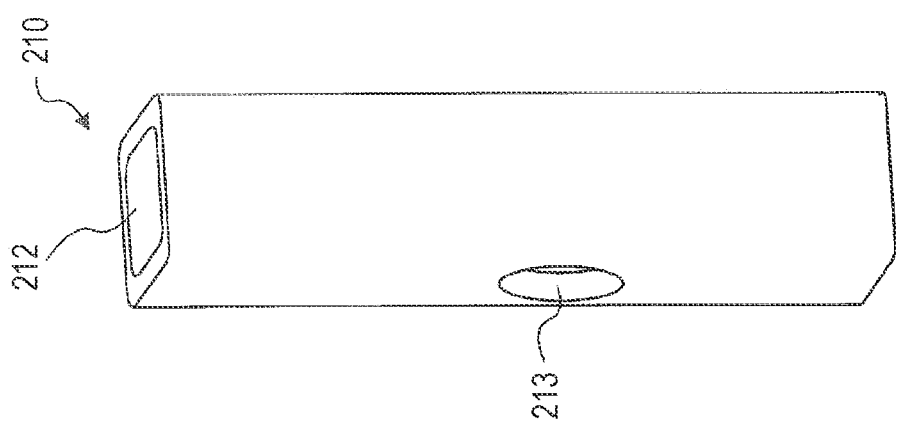
FIG. 2B is a perspective view of a well body.
Figure 2A:
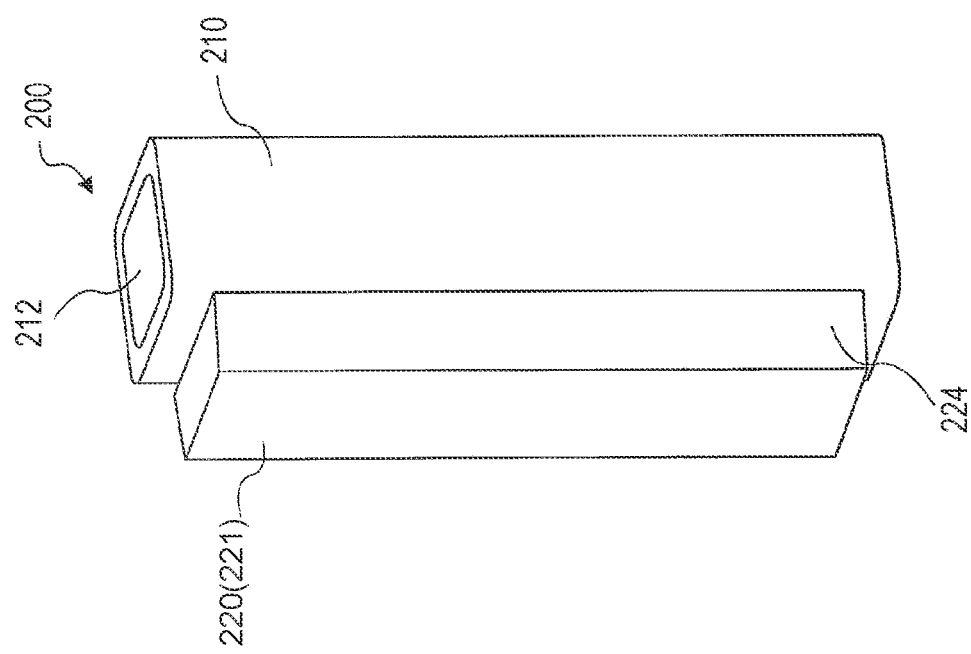
FIG. 2A is a perspective view of a detection chip according to the first embodiment.
Figure 3A:
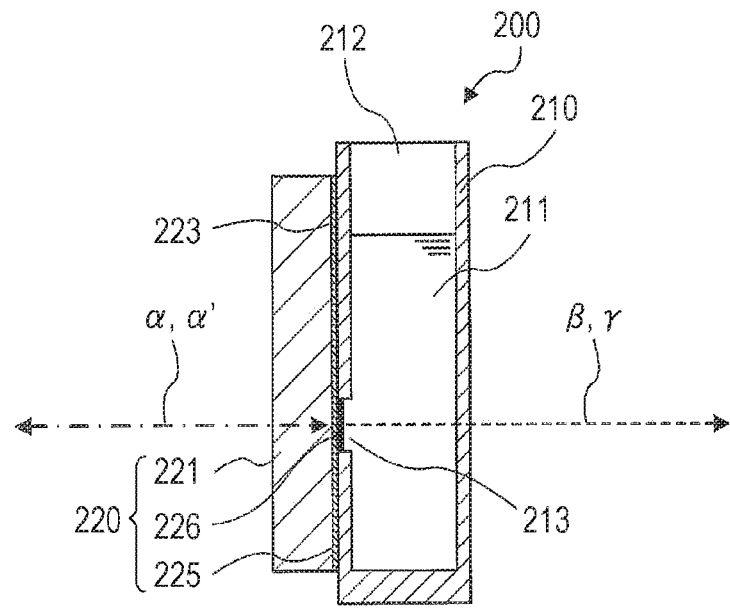
FIGS. 3A and 3B are schematic diagrams showing light entering the detection chip and light emitted from the detection chip according to the first embodiment.
Figure 3B:
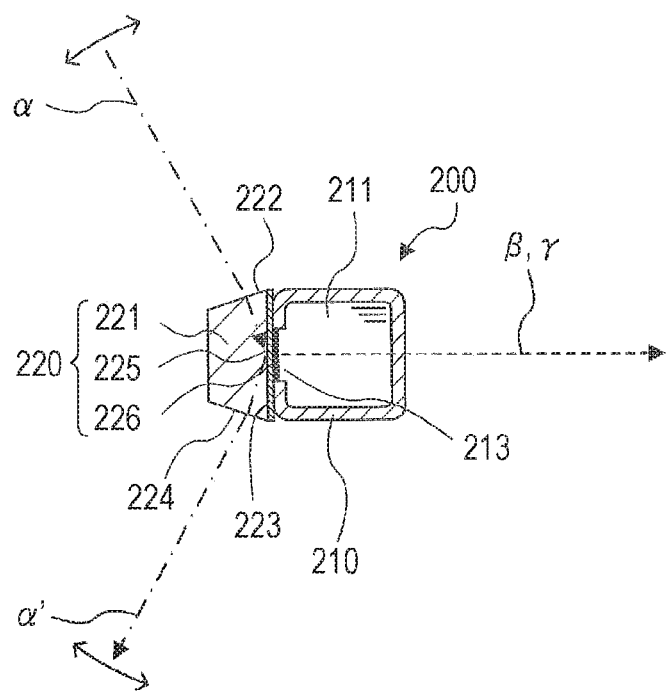
Figure 4:
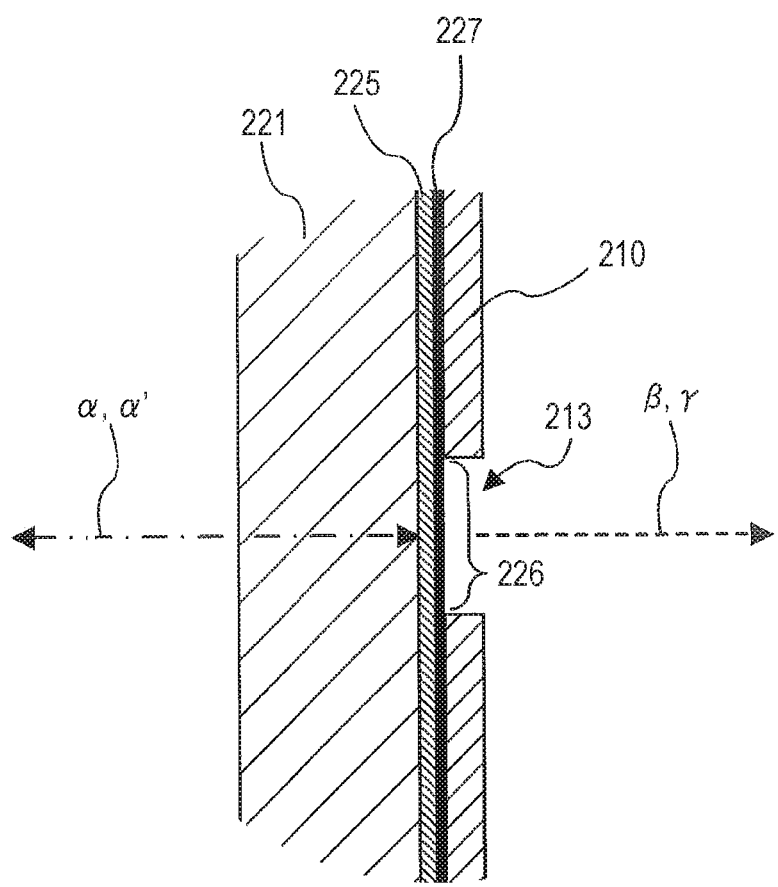
FIG. 4 is a partially enlarged cross-sectional view enlarging the vicinity of a reaction field in the cross-sectional view of FIG. 3A.

FIGS. 2A to 2C are schematic diagrams showing a configuration of the detection chip 200 according to the first embodiment. FIG. 2A is a perspective view of the detection chip 200, FIG. 2B is a perspective view of a well body 210, and FIG. 2C is a perspective view of the well body 210. FIGS. 3A and 3B are schematic diagrams showing light (excitation light α) entering the detection chip 200 and light (fluorescence β and plasmon scattered light γ) emitted from the detection chip 200. FIG. 3A is a cross-sectional view along the height direction of the detection chip 200, and FIG. 3B is a cross-sectional view along the horizontal direction of the detection chip 200. FIGS. 3A and 3B show a state in which a liquid (for example, a measurement buffer solution) is housed in a housing 211. FIG. 4 is a partially enlarged cross-sectional view enlarging the vicinity of a reaction field 226 in the cross-sectional view of FIG. 3A.

As shown in FIGS. 2A, 3A and 3B, the detection chip 200 has the well body 210 and a side wall member 220.

The well body 210 has a housing (well) 211 therein. The housing 211 is a bottomed recessed portion configured to be capable of housing liquid, and is opened to the outside in a first opening 212 provided in the upper portion and a second opening 213 provided in the side portion. The first opening 212 is used for introducing the liquid into the housing 211 or removing the liquid in the housing 211. The second opening 213 is formed to form the reaction field 226 by exposing a trapping region 227 of the side wall member 220, which will be described later, into the housing 211 (see FIG. 4). The second opening 213 is closed by the side wall member 220 so as to house the liquid in the housing 211. In the present embodiment, as shown in FIGS. 2B and 2C, the second opening 213 is a through hole formed in the side wall on the side of the side wall member 220 among the four side walls included in the housing 211.

Figure 5A:
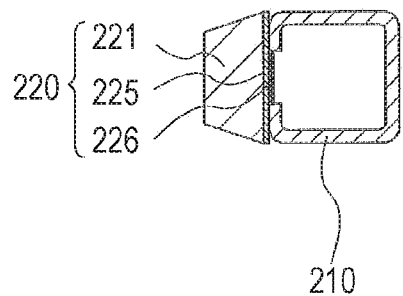
FIGS. 5A to 5D are cross-sectional views of the detection chip showing an example of a shape of a side wall opposed to the reaction field.
Figure 5B:
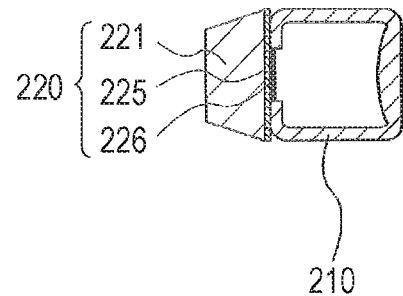
Figure 5C:
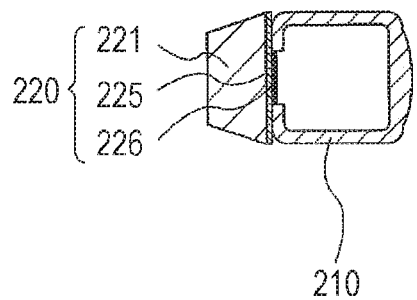
Figure 5D:
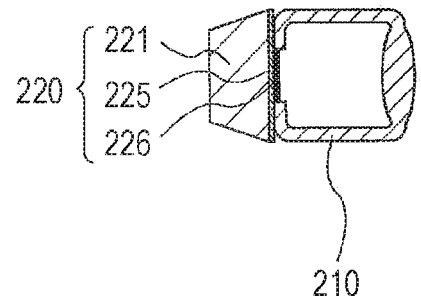

In the detection chip 200 according to the present embodiment, the light (fluorescence β and plasmon scattered light γ) emitted from the vicinity of the reaction field 226 passes through the side wall opposed to the reaction field 226 and is detected by a detection unit 125 described later (see FIG. 1). Accordingly, when it is desired to suppress the refraction of the light to be detected, as shown in FIG. 5A, it is preferable that both the inner surface and the outer surface of the side wall opposed to the reaction field 226 (trapping region 227) in the housing are flat. On the other hand, as shown in FIGS. 5B to D, when it is desired to collect light to be detected to the detection unit 125, it is preferable that at least one of the inner surface and the outer surface of the side wall opposed to the reaction field 226 in the housing is formed as a convex curved surface. In the example shown in FIG. 5B, only the inner surface of the side wall is a convex curved surface, and the side wall opposed to the reaction field 226 functions as a plano-convex cylindrical lens. In the example shown in FIG. 5C, only the outer surface of the side wall is a convex curved surface, and the side wall opposed to the reaction field 226 functions as a plano-convex cylindrical lens. In the example shown in FIG. 5D, both the inner surface and the outer surface of the side wall are convex curved surfaces, and the side wall opposed to the reaction field 226 functions as a biconvex cylindrical lens.

Figure 6A:
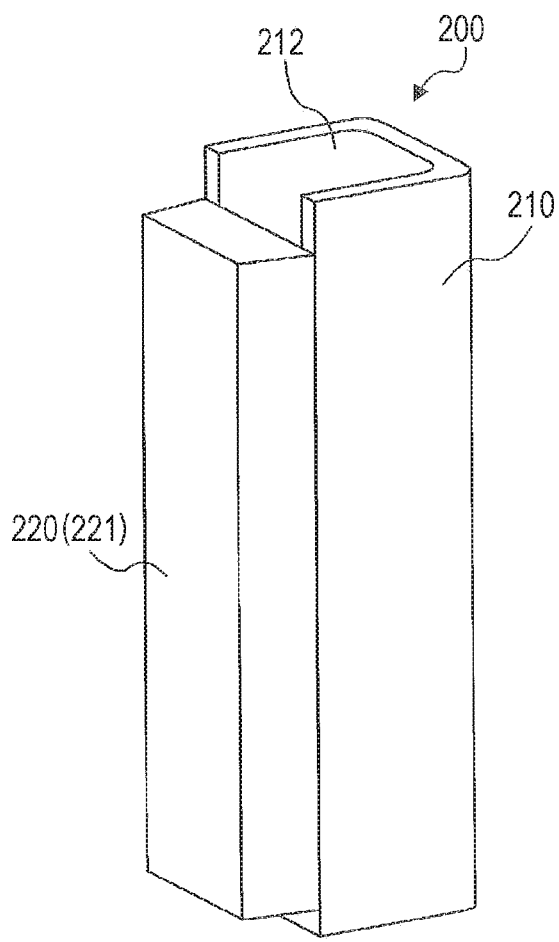
FIG. 6A is a perspective view of a detection chip according to a first modification.
Figure 6B:
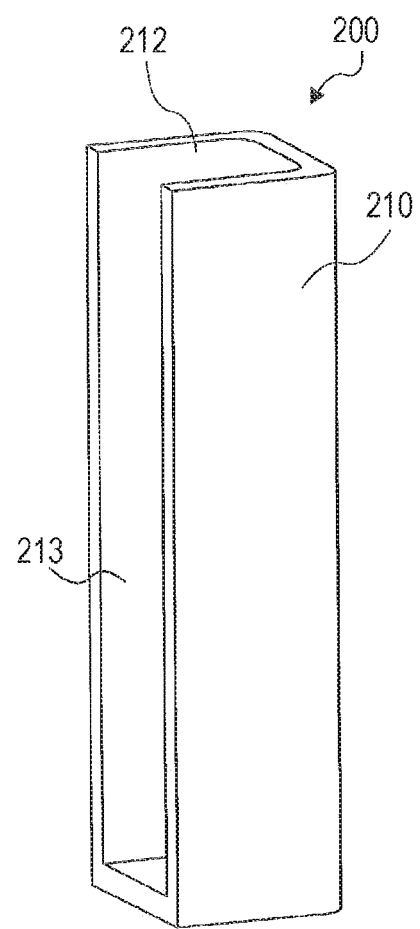
FIG. 6B is a perspective view of a well body according to the first modification.

The shape of the well body 210 is not particularly limited as long as the well body 210 has the housing 211, the first opening 212, and the second opening 213. FIG. 6A is a perspective view of the detection chip 200 according to a first modification, and FIG. 6B is a perspective view of the well body 210 according to the first modification. For example, as shown in FIGS. 6A and 6B, the second opening 213 may be formed on the entire surface on the side wall member 220 side or may be connected to the first opening 212. Also in this case, at least a part of the second opening 213 is closed by the side wall member 220 so as to house the liquid in the housing 211.

Figure 7A:
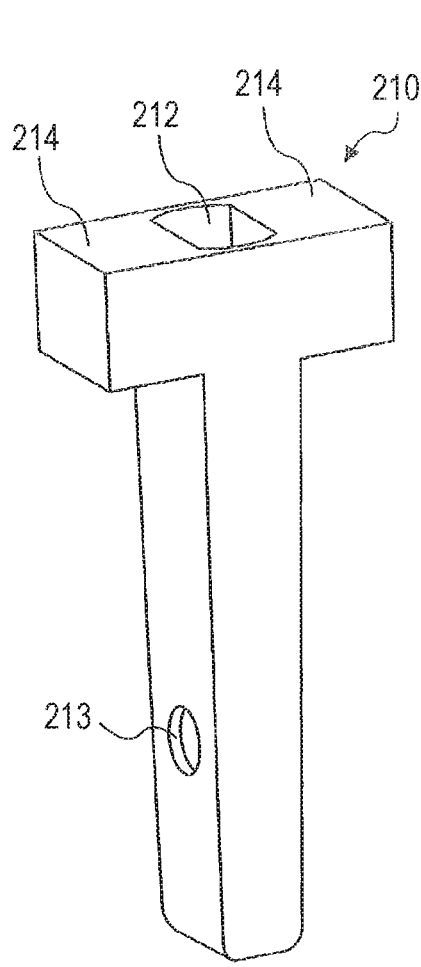
FIG. 7A is a perspective view of a well body according to a second modification.
Figure 7B:
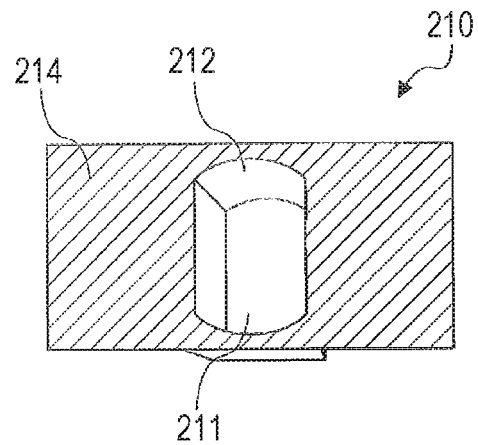
FIG. 7B is a cross-sectional view along a horizontal direction of the well body according to the second modification.
Figure 7C:
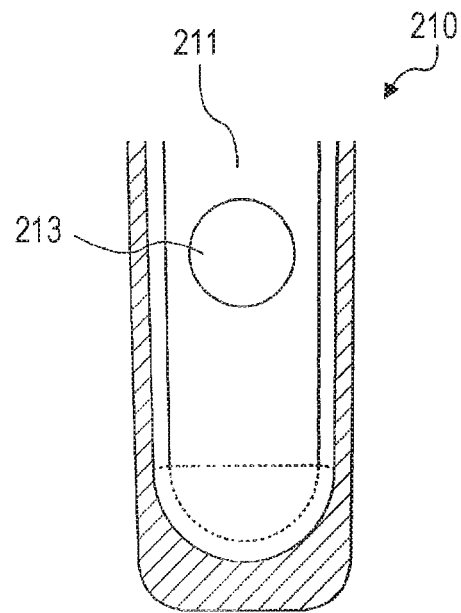
FIG. 7C is a cross-sectional view along the height direction in the vicinity of a bottom portion of the well body according to the second modification.

FIG. 7A is a perspective view of the well body 210 according to a second modification, FIG. 7B is a cross-sectional view along a horizontal direction of the well body 210 according to the second modification, and FIG. 7C is a cross-sectional view along the height direction in the vicinity of a bottom portion of the well body 210 according to the second modification. For example, as shown in FIG. 7A, the well body 210 may further include a holding unit 214 protruding sideways from the top thereof. When the detection chip 200 has the holding unit 214 in such a manner, since a user and a system can grasp the holding unit, handling of the detection chip 200 becomes easier. As shown in FIG. 7B, among the four side walls included in the housing 211, all or a part of the inner surface of the side wall other than the side wall opposed to the reaction field 226 may be a curved surface curved in the circumferential direction. With such a configuration, when circumferential rotational vibration is applied to the detection chip 200, it is possible to efficiently agitate the liquid in the housing 211. Note that, when reciprocating vibration in the horizontal direction is applied to the detection chip 200, it is preferable that the cross-sectional shape along the horizontal direction of the housing 211 is substantially polygonal (for example, substantially square shape) (see FIG. 3B). As shown in FIG. 7C, the bottom portion of the housing 211 may have a downwardly convex shape (for example, a round bottom). With such a configuration, it is possible to more reliably remove the liquid in the housing 211, and it is possible to improve the detection accuracy.

The well body 210 is formed of a material transparent to light (at least light having the wavelength of the excitation light α and light having the wavelength of the fluorescence β). However, a part of the well body 210 may be formed of a material opaque to light as long as the material does not hinder the light extraction in the detection method described later. At least the side wall opposed to the reaction field 226, among the four side walls included in the housing 211 has optical transparency. Examples of the material transparent to light include a resin and a glass.

The side wall member 220 has a prism 221 as an optical element, the metal film 225, and the reaction field 226. Here, the "reaction field" means a region in the trapping region 227 arranged on the metal film 225, the region exposed in the housing 211 via the second opening 213 (see FIG. 4). As shown in FIGS. 2A, 3A, 3B, and 4, the side wall member 220 is fixed to the well body 210 such that at least a part of the trapping region 227 is exposed into the housing 211 to be the reaction field 226, and the side wall member 220 completely closes at least a part of the second opening 213. In the present embodiment, the side wall member 220 adheres to the well body 210 via an adhesive layer (not shown) such as a double-faced tape so as to close the entire second opening 213. The side wall member 220 may be joined to the well body 210 by laser welding, ultrasonic welding, crimping using a clamp member, or the like without using an adhesive layer.

The prism 221 is an optical element made of a dielectric transparent to the excitation light α, and has an entrance surface 222, a reflection surface 223, and an exit surface 224, as shown in FIG. 3B. The prism 221 also functions as a side wall included in the housing 211. The entrance surface 222 is a surface for causing the excitation light α from the excitation light irradiation unit 110 to enter the inside of the prism 221. The excitation light α that has entered the inside of the prism 221 is reflected by the reflection surface 223. As will be described later, the metal film 225 and the trapping region 227 are arranged in order on the reflection surface 223. The exit surface 224 is a surface for causing the reflected light α' reflected by the reflection surface 223 to be emitted to the outside of the prism 221.

The shape of the prism 221 is not particularly limited, but the reflection surface 223 is preferably flat. Examples of the shape of the prism 221 include a columnar body having a trapezoid as a bottom surface, a triangular column, and a semicircular column. In the present embodiment, the shape of the prism 221 is a columnar body having a trapezoid as a bottom surface. The surface corresponding to one base of the trapezoid is the reflection surface 223, the surface corresponding to one leg is the entrance surface 222, and the surface corresponding to the other leg is the exit surface 224.

The entrance surface 222 is formed such that the excitation light α does not return to the excitation light irradiation unit 110. In the case where the light source of the excitation light α is a laser diode (hereinafter also referred to as "LD"), when the excitation light α returns to the LD, the excited state of the LD is disturbed, and the wavelength and output of the excitation light α vary. Therefore, in a scanning range centered on the ideal resonance angle or enhancement angle, the angle of the entrance surface 222 is set such that the excitation light α does not enter the entrance surface 222 perpendicularly. Here, the "resonance angle" means an incident angle at the time when the light amount of the reflected light α emitted from the exit surface 224 is the minimum in a case where the incident angle of the excitation light α with respect to the reflection surface 223 (the metal film 225) is scanned. The "enhancement angle" means an incident angle at the time when the light amount of the scattered light (plasmon scattered light) γ having the same wavelength as the excitation light α emitted from the vicinity of the reaction field 226 into the housing 211 is the maximum in a case where the incident angle of the excitation light α with respect to the reflection surface 223 (the metal film 225) is scanned. In the present embodiment, the angle between the entrance surface 222 and the reflection surface 223 and the angle between the reflection surface 223 and the exit surface 224 are both about 80°.

By the design of the detection chip 200, the resonance angle (and the enhancement angle in the immediate vicinity thereof) is roughly determined. The design elements are the refractive index of the prism 221, the refractive index of the metal film 225, the film thickness of the metal film 225, the extinction coefficient of the metal film 225, the wavelength of the excitation light α, and the like. The resonance angle and the enhancement angle are shifted by the substance to be detected trapped in the reaction field 226 (trapping region 227) on the metal film 225, and the shift amount is less than several degrees.

The prism 221 has not a few birefringence characteristics. Examples of the material of the prism 221 include a resin and a glass. The material of the prism 221 is preferably a resin having a refractive index of 1.4 to 1.6 and a small birefringence.

The metal film 225 is arranged on the reflection surface 223 of the prism 221. As a result, an interaction (SPR) occurs between a photon of the excitation light α incident on the reflection surface 223 under the total reflection condition and a free electron in the metal film 225, and the enhancement electric field localized on the surface of the metal film 225 is generated.

The material of the metal film 225 is not particularly limited as long as the material is a metal capable of causing surface plasmon resonance. Examples of the material of the metal film 225 include gold, silver, copper, aluminum, and alloys thereof. The method for forming the metal film 225 is not particularly limited. Examples of a method of forming the metal film 225 include sputtering, vapor deposition, and plating. The thickness of the metal film 225 is not particularly limited, but it is preferably within the range of 30 to 70 nm.

The reaction field 226 is a region for trapping the substance to be detected that is exposed in the housing 211. As described above, the reaction field 226 means a region in the trapping region 227 arranged on the metal film 225, the region exposed in the housing 211 via the second opening 213. As shown in FIG. 4, when the size of the trapping region 227 is such a size capable of closing the second opening 213, the range of the reaction field 226 is defined by the second opening 213. With such a configuration, it is possible to adjust the size of the reaction field 226 with high accuracy and with ease. On the other hand, as shown in FIG. 6B, when the size of the second opening 213 is larger (than the trapping region 227), a trapping region 227 having a predetermined shape is formed on a part of the surface of the metal film 225, and the trapping region 227 becomes the reaction field 226 as it is.

The reaction field 226 is arranged on the inner side surface of the housing 211. At this time, it is preferable that the reaction field 226 is arranged at a position away from the deepest portion of the housing 211. By adopting such a configuration, it is possible to efficiently generate a reaction in the reaction field 226 when an analyte or the like is introduced into the housing 211. It is also possible to suppress noise caused by the bottom portion of the housing 211 from being mixed in the detection result at the time of detecting the fluorescence β.

The trapping region 227 is the region in which a first trapping body for trapping a substance to be detected on the metal film 225 is immobilized. The first trapping body is a substance having a recognition site for specifically binding with a substance to be detected in the analyte. If the first trapping body is immobilized to the reaction field 226 (trapping region 227), when the analyte is introduced into the housing 211, the substance to be detected is selectively bound to the first trapping body. That is, the substance to be detected is trapped in the reaction field 226. This makes it possible to detect the substance to be detected as described later. The type of the first trapping body is not particularly limited as long as the first trapping body has a recognition site for specifically binding to the substance to be detected. Examples of the first trapping body include an antibody (primary antibody) or a fragment thereof capable of specifically binding to the substance to be detected, an enzyme capable of specifically binding to the substance to be detected, and the like.

From the viewpoint of improving detection accuracy, it is preferable that the surface on which the trapping region 227 is arranged in the region to be the reaction field 226 is flat. That is, in the case where the trapping region 227 is arranged on the metal film 225 as in the present embodiment, the surface of the metal film 225 is preferably flat. As described at the end of the present embodiment, in the case where the trapping region 227 is arranged on the reflection surface 223, the reflection surface 223 is preferably flat.

Figure 8A:
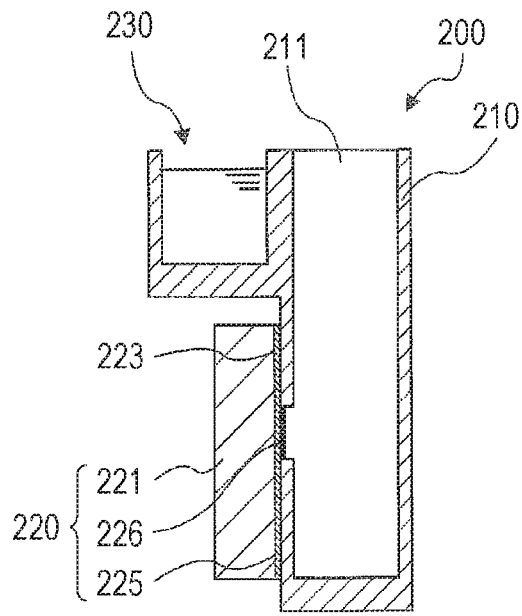
FIGS. 8A to 8C are cross-sectional views showing an example of a detection chip having a plurality of housings.
Figure 8B:
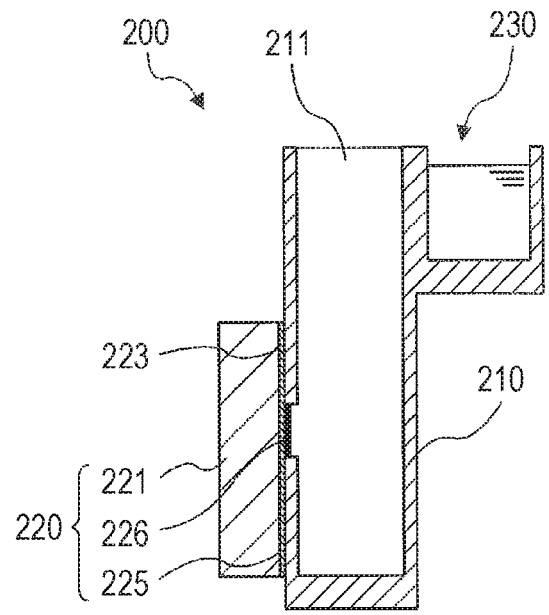
Figure 8C:
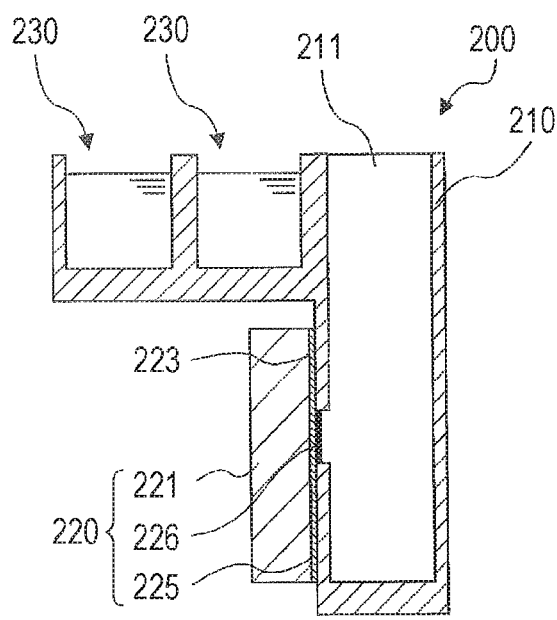

As shown in FIGS. 8A to 8C, the detection chip 200 may further include a second housing 230 that can house liquid in addition to the housing 211. The use of the second housing 230 is not particularly limited. For example, reagents used in the reaction step or the detection step may be housed in advance in the second housing 230. In the reaction step or the detection step, two or more types of reagents may be mixed in the second housing 230. The number of the second housings 230 and the position of the second housing 230 are not particularly limited as long as they do not hinder the detection of the substance to be detected. For example, as shown in FIG. 8A, one second housing 230 may be added to the side wall on the side wall member 220 side in the four side walls included in the housing 211. As shown in FIG. 8B, one second housing 230 may be added to the side wall opposed to the reaction field 226 in the four side walls included in the housing 211. As shown in FIG. 8C, a plurality of second housings 230 may be added to one side wall among the four side walls included in the housing 211. As shown in these drawings, when the second housing 230 is added to the side wall on the side wall member 220 side or the side wall opposed to the reaction field 226 in the four side walls included in the housing 211, the detection chip 200 has a substantially rectangular shape in plan view, and the plurality of detection chips 200 can be housed efficiently in a housing container.

(Detection System)

Next, components other than the detection chip 200 of the detection system 100 will be described. As described above, in addition to the detection chip 200, the detection system 100 includes an excitation light irradiation unit 110, a fluorescence detection unit 120, a liquid transfer unit 130, a vibration unit 140, and a control unit 150 (see FIG. 1).

The excitation light irradiation unit 110 irradiates the detection chip 200 with the excitation light $\alpha$. In the measurement of the fluorescence $\beta$ or the plasmon scattered light $\gamma$, the excitation light irradiation unit 110 emits only the P wave with respect to the reflection surface 223 (the metal film 225) to the entrance surface 222 of the prism 221 such that the incident angle with respect to the reflection surface 223 (the metal film 225) of the prism 221 is the angle at which the SPR occurs in the metal film 225. Here, the "excitation light" is light that directly or indirectly excites a fluorescent substance. For example, the excitation light $\alpha$ is light that generates an enhancement electric field for exciting a fluorescent substance on the surface of the metal film 225 when the reflection surface 223 (the metal film 225) is irradiated with the excitation light $\alpha$ via the prism 221 at the angle at which the SPR occurs in the metal film 225. The excitation light irradiation unit 110 includes a light source unit 111 and a first angle adjustment unit 112.

The light source unit 111 emits the excitation light $\alpha$ that is collimated and has constant wavelength and light amount such that the shape of the irradiation spot on the reflection surface 223 (the surface of the metal film 225) is substantially circular. The size of the irradiation spot is preferably smaller than the reaction field 226 of the detection chip 200. The light source unit 111 includes, for example, a light source of the excitation light $\alpha$, a beam shaping optical system, an APC mechanism, and a temperature adjustment mechanism (none of them are shown).

The type of the light source is not particularly limited, and is, for example, a laser diode (LD). Other examples of the light source include a light emitting diode, a mercury lamp, and other laser light sources. When the light emitted from the light source is not a beam, the light emitted from the light source is converted into a beam by a lens, a mirror, a slit or the like. When the light emitted from the light source is not a monochromatic light, the light emitted from the light source is converted into a monochromatic light by a diffraction grating or the like. When the light emitted from the light source is not a linearly polarized light, the light emitted from the light source is converted into a linearly polarized light by a polarizer or the like.

The beam shaping optical system includes, for example, a collimator, a band pass filter, a linear polarization filter, a half wave plate, a slit, a zoom means, and the like. The beam shaping optical system may include all or some of them. The collimator collimates the excitation light $\alpha$ emitted from the light source. The band pass filter converts the excitation light $\alpha$ emitted from the light source into narrow band light having only the center wavelength. This is because the excitation light $\alpha$ from the light source has a slight wavelength distribution width. The linear polarization filter converts the excitation light $\alpha$ emitted from the light source into completely linearly polarized light. The half wave plate adjusts the polarization direction of the excitation light $\alpha$ such that the P wave component enters the reflection surface 223. The slit and the zoom means adjust the beam diameter and contour shape of the excitation light $\alpha$ such that the shape of the irradiation spot on the reflection surface 223 is a circle having a predetermined size.

The APC mechanism controls the light source such that the output of the light source is constant. More specifically, the APC mechanism detects the light amount of the light branched from the excitation light $\alpha$ with a photodiode (not shown) or the like. The APC mechanism controls the input energy by the regression circuit, thereby controlling the output of the light source to be constant.

The temperature adjustment mechanism is, for example, a heater or a Peltier element. The wavelength and the energy of the light emitted from the light source may vary depending on the temperature. For this reason, the temperature adjustment mechanism keeps the temperature of the light source constant, so that the wavelength and the energy of the light emitted from the light source are controlled to be constant.

The first angle adjustment unit 112 adjusts the incident angle of the excitation light $\alpha$ to the reflection surface 223. In order to irradiate the predetermined position on the reflection surface 223 with the excitation light a at a predetermined incident angle via the prism 221, the first angle adjustment unit 112 rotates the optical axis of the excitation light $\alpha$ and the detection chip 200 relative to each other.

For example, the first angle adjustment unit 112 rotates the light source unit 111 around an axis orthogonal to the optical axis of the excitation light $\alpha$ (an axis along the height direction of the detection chip 200) (see FIG. 3B). At this time, the position of the rotation axis is set such that the position of the irradiation spot on the reflection surface 223 hardly changes even if the incident angle is scanned.

As described above, the angle at which the light amount of the plasmon scattered light $\gamma$ is maximum among the incident angles of the excitation light $\alpha$ with respect to the reflection surface 223 (the metal film 225) is the enhancement angle. It is possible to measure the high intensity fluorescence $\beta$ by setting the incident angle of the excitation light $\alpha$ at or near the enhancement angle (for example, the resonance angle). The basic incident condition of the excitation light $\alpha$ is determined by the material and shape of the prism 221 of the detection chip 200, the film thickness of the metal film 225, the refractive index of the liquid in the housing 211, and the like. However, the optimum incident condition varies slightly by the type and amount of the fluorescent substance to be used, the shape error of the prism 221, or the like. Therefore, it is preferable to determine an optimum enhancement angle for each detection.

The fluorescence detection unit 120 detects the fluorescence β generated by the irradiation of the excitation light α to the reflection surface 223 (the metal film 225). The fluorescence detection unit 120 also detects the plasmon scattered light γ generated by the irradiation of the excitation light α to the reflection surface 223 (the metal film 225) as needed. The fluorescence detection unit 120 includes a first lens 121, an optical filter 122, a second lens 123, a position switching unit 124, and a detection unit 125.

The first lens 121 is, for example, a condenser lens and condenses light emitted from the vicinity of the reaction field 226. The second lens 123 is, for example, an imaging lens, and focuses the light condensed by the first lens 121 on the light receiving surface of the detection unit 125. An optical path between both lenses is a substantially parallel optical path. The optical filter 122 is arranged between both lenses.

The optical filter 122 directs only the fluorescence component to the detection unit 125, and removes the excitation light component (plasmon scattered light γ) in order to detect the fluorescence β with a high signal (S)/noise (N) ratio. Examples of the optical filter 122 include an excitation light reflection filter, a short wavelength cut filter, and a band pass filter. The optical filter 122 is, for example, a filter including a multilayer film that reflects a predetermined light component, or a color glass filter that absorbs a predetermined light component.

The position switching unit 124 switches the position of the optical filter 122 on the optical path between the first lens 121 and the second lens 123 or outside the optical path. Specifically, when the detection unit 125 detects the fluorescence β, the optical filter 122 is arranged on the optical path, and when the detection unit 125 detects the plasmon scattered light γ, the optical filter 122 is arranged outside the optical path.

The detection unit 125 is a light receiving sensor for detecting the fluorescence β and the plasmon scattered light γ. The detection unit 125 has a high sensitivity capable of detecting weak fluorescence β from a minute amount of a substance to be detected. The detection unit 125 is, for example, a photomultiplier tube (PMT) or an avalanche photodiode (APD).

As shown in FIG. 1 and FIG. 3A, in the present embodiment, the excitation light α from the light source unit 111 travels in the horizontal direction and reaches the detection chip 200. The light (fluorescence β and plasmon scattered light γ) emitted from the vicinity of the reaction field 226 and traveling in the horizontal direction is detected by the detection unit 125. Accordingly, in the present embodiment, the light source unit 111 and the detection unit 125 are arranged at the same height as the detection chip 200. Of course, if a mirror or the like is used, the positions of the light source unit 111 and the detection unit 125 can be freely changed. However, from the viewpoint of miniaturization, it is preferable that the light source unit 111 and the detection unit 125 are arranged at the same height as the detection chip 200.

The liquid transfer unit 130 introduces various liquids into the housing 211 of the detection chip 200. The liquid transfer unit 130 removes various liquids from the inside of the housing 211 of the detection chip 200. In the present embodiment, the liquid transfer unit 130 injects or sucks, for example, an analyte, a labeling solution including a second trapping body labeled with a fluorescent substance (hereinafter also referred to as "labeling solution"), a washing solution, a measuring buffer solution, or the like. The liquid transfer unit 130 includes a liquid chip 131, a pipette 132, and a pipette control unit 136.

The liquid chip 131 is a container for housing liquid such as an analyte, a labeling solution, a washing solution, and a measuring buffer solution. As the liquid chip 131, generally, a plurality of containers are arranged according to the type of liquid, or a chip in which a plurality of containers are integrated is arranged. Note that, as shown in FIGS. 8A to 8C, when the detection chip 200 has the second housing 230, the second housing 230 can function as the liquid chip 131. In this case, the liquid transfer unit 130 may not have the liquid chip 131.

The pipette 132 has a syringe pump 133, a nozzle unit 134 connected to the syringe pump 133, and a pipette tip 135 mounted to the tip of the nozzle unit 134. By the reciprocating motion of the plunger in the syringe pump 133, the liquid is sucked and discharged in the pipette tip 135 quantitatively.

The pipette control unit 136 includes a driving device for the syringe pump 133 and a moving device for the nozzle unit 134. The driving device for the syringe pump 133 is a device for reciprocating the plunger of the syringe pump 133 and includes, for example, a stepping motor. For example, the moving device for the nozzle unit 134 moves the nozzle unit 134 freely in two directions, that is, a vertical direction and a horizontal direction. The moving device for the nozzle unit 134 includes, for example, a robot arm, a biaxial stage, or a vertically movable turntable.

The pipette control unit 136 drives the syringe pump 133 to suck various types of liquid from the liquid chip 131 into the pipette tip 135. The pipette control unit 136 then moves the nozzle unit 134 to cause the pipette tip 135 to be inserted from the first opening 212 into the housing 211 of the detection chip 200, and drives the syringe pump 133 to inject the liquid in the pipette tip 135 into the housing 211. After the introduction of the liquid, the pipette control unit 136 drives the syringe pump 133 to suck the liquid in the housing 211 into the pipette tip 135. The liquid in the housing 211 is sequentially exchanged in this way, so that the first trapping body and the substance to be detected are reacted with each other in the reaction field 226 (primary reaction), or the substance to be detected and the second trapping body labeled with the fluorescent substance are reacted with each other (secondary reaction).

The vibration unit 140 vibrates the detection chip 200 in order to agitate the liquid in the housing 211. In this manner, the detection chip 200 is vibrated and the liquid in the housing 211 is agitated, so that it is possible to efficiently perform the primary reaction, the secondary reaction, the cleaning, or the like in the reaction field 226. The vibration unit 140 is, for example, a piezo element or an eccentric rotating body. The vibration unit 140 is arranged at a position that does not hinder the optical paths of the excitation light α, the fluorescence β, and the plasmon scattered light γ.

The direction of vibration applied to the detection chip 200 by the vibration unit 140 is not particularly limited. Examples of the vibration direction include a horizontal direction, a vertical direction (height direction), a circumferential direction, and the like. For example, reciprocating vibration in the horizontal direction can be applied to the detection chip 200 by driving the piezo element in a state where the piezo element as the vibration unit 140 is in contact with the side surface of the detection chip 200. In addition, reciprocating vibration in the vertical direction can be applied to the detection chip 200 by driving the piezo element in a state where the piezo element as the vibration unit 140 is in contact with the bottom surface of the detection chip 200. In addition, rotation vibration in the circumferential direction can be applied to the detection chip 200 by rotating a rotating body in a state where the eccentric rotating body as the vibration unit 140 is in contact with the bottom surface of the detection chip 200. From the viewpoint of efficiently agitating the liquid in the housing 211, it is preferable to vibrate the detection chip 200 with the natural frequency of the detection chip 200 in a state where the liquid is housed in the housing 211, or the vibration frequency in the periphery thereof. The detection chip 200 may be vibrated while sequentially switching different natural frequencies (n-th natural frequency and m-th natural frequency, n and m are positive integers).

The control unit 150 controls the light source unit 111, the first angle adjustment unit 112, the position switching unit 124, the detection unit 125, the pipette control unit 136, and the vibration unit 140. The control unit 150 includes, for example, a well-known computer or a microcomputer including an arithmetic device, a control device, a storage device, an input device, and an output device.

In the present embodiment, the liquid transfer unit 130 and the vibration unit 140 are arranged such that introduction and removal of liquid by the liquid transfer unit 130 and application of vibration by the vibration unit 140 are performed on the detection chip 200 arranged at a position where the detection chip 200 can be irradiated with the excitation light α. However, the positions of the liquid transfer unit 130 and the vibration unit 140 are not limited thereto. For example, when the detection chip 200 is arranged at a first position, introduction and removal of liquid by the liquid transfer unit 130 and application of vibration by the vibration unit 140 may be performed, and when the detection chip 200 is arranged at a second position, irradiation with the excitation light α by the excitation light irradiation unit 110 and the detection of the fluorescence β by the fluorescence detection unit 120 may be performed. In this case, the detection system 100 further includes a conveyance unit for moving the detection chip 200 to the first position and the second position.

(Detection Method)

Figure 9:
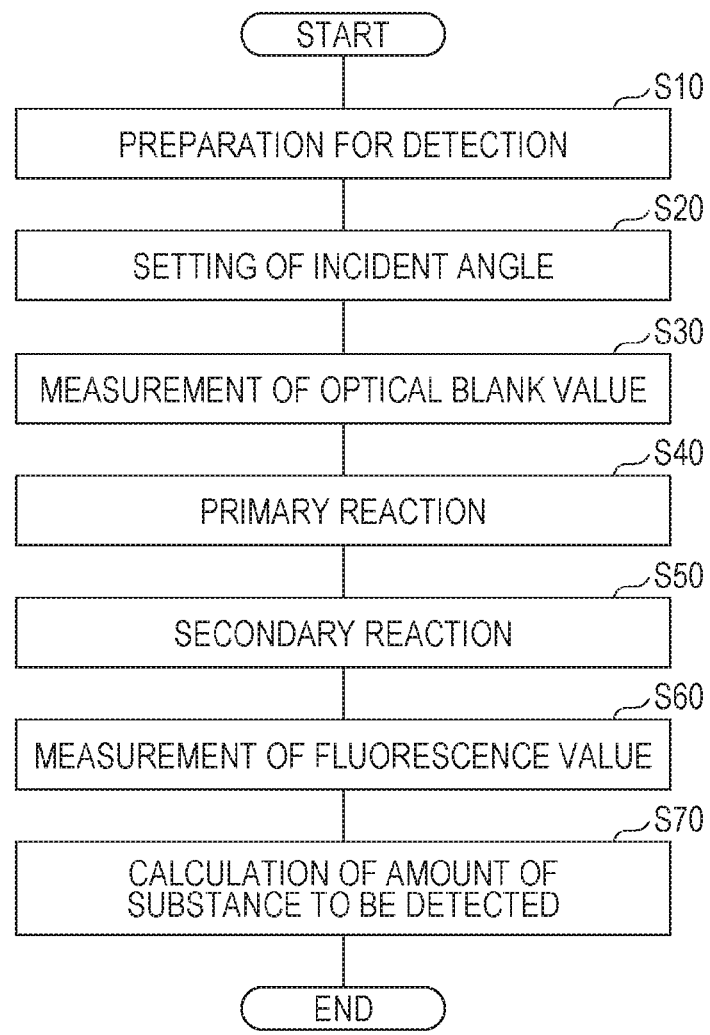
FIG. 9 is a flowchart of a detection method according to the first embodiment, and is a flowchart showing an example of an operation procedure of a detection system.

Next, a detection method of a substance to be detected using the detection system 100 will be described. FIG. 9 is a flowchart showing an example of an operation procedure of the detection system 100 in performing the detection method according to the present embodiment.

First, preparation for detection is performed (step S10). Specifically, the detection chip 200 is installed at a predetermined position of the detection system 100. In the case where a humectant is present on the reaction field 226 of the detection chip 200, the interior of the housing 211 is washed to remove the humectant on the reaction field 226. Thereafter, the control unit 150 controls the pipette control unit 136 to introduce the measurement buffer solution into the housing 211.

Next, the incident angle of the excitation light α to the reflection surface 223 (the metal film 225) of the detection chip 200 is set as the enhancement angle (step S20). Specifically, the control unit 150 controls the light source unit 111 and the first angle adjustment unit 112 to cause the position corresponding to the reaction field 226 of the reflection surface 223 to be irradiated with the excitation light α, while scanning the incident angle of the excitation light α with respect to the reflection surface 223. At the same time, the control unit 150 controls the detection unit 125 to detect the plasmon scattered light γ. At this time, the control unit 150 controls the position switching unit 124 to move the optical filter 122 out of the optical path. The control unit 150 obtains data including the relationship between the incident angle of the excitation light α and the intensity of the plasmon scattered light γ. The control unit 150 analyzes the data and determines an incidence angle (enhancement angle) at which the intensity of the plasmon scattered light γ becomes maximum Finally, the control unit 150 controls the first angle adjustment unit 112 to set the incident angle of the excitation light α to the reflection surface 223 to the enhancement angle.

The enhancement angle is determined by the material and shape of the prism 221, the thickness of the metal film 225, the refractive index of the liquid in the housing 211, and the like, but varies slightly depending on various factors such as the type and amount of liquid in the housing 211, or shape error of the prism 221. For this reason, it is preferable to determine the enhancement angle each time detection is performed. The enhancement angle is determined on the order of about 0.1°.

Next, an optical blank value is measured (step S30). Specifically, the control unit 150 controls the light source unit 111 to irradiate a position corresponding to the reaction field 226 of the reflection surface 223 with the excitation light α. At the same time, the control unit 150 controls the detection unit 125 to detect the light amount of background light having the same wavelength as the fluorescence β. At this time, the control unit 150 controls the position switching unit 124 to move the optical filter 122 on the optical path. The control unit 150 records the measured light amount of the background light as a blank value.

Figure 10A:
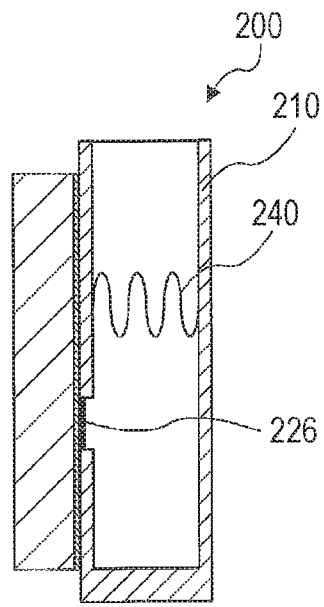
FIGS. 10A and 10B are schematic diagrams showing a relationship between a reaction field and a liquid surface when a detection chip is vibrated.
Figure 10B:
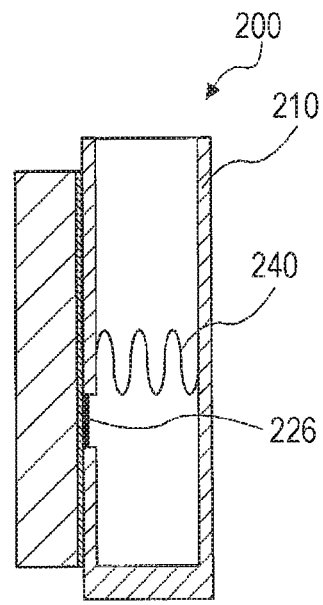

Next, an analyte is introduced into the housing 211 of the detection chip 200, and the substance to be detected contained in the analyte is specifically bound to the first trapping body in the reaction field 226 (primary reaction (step S40)). Specifically, the control unit 150 controls the pipette control unit 136 to remove the measurement buffer solution in the housing 211 and to introduce the analyte into the housing 211. The control unit 150 controls the vibration unit 140 to vibrate the detection chip 200 to agitate the analyte in the housing 211. At this time, from the viewpoint of appropriately proceeding the reaction, as shown in FIGS. 10A and 10B, it is preferable that the reaction field 226 is always below the vibrating liquid surface 240 of the liquid (analyte) in the housing 211. From the viewpoint of increasing the reaction efficiency, it is more preferable that the reaction field 226 is closer to the vibrating liquid surface 240 compared with the case of FIG. 10A, as shown in FIG. 10B. From the viewpoint of preventing the scattering of the liquid (analyte), it is preferable that the height of the liquid surface 240 in a state of being standing is ⅔ or less of the depth (height) of the housing 211, and more preferably 1/2 or less. Thereafter, the control unit 150 controls the pipette control unit 136 to remove the analyte in the housing 211, introduce the washing solution into the housing 211, and wash the interior of the housing 211. Also at this time, the control unit 150 controls the vibration unit 140 to vibrate the detection chip 200 to agitate the washing solution in the housing 211.

The types of the analyte and the substance to be detected are not particularly limited. Examples of the analyte include body fluids such as blood and serum, plasma, cerebrospinal fluid, urine, nostrils, saliva, or semen, tissue extracts, and dilutions thereof. Examples of the substance to be detected contained in these analytes include nucleic acids (DNA, RNA, or the like), proteins (polypeptides, oligopeptides, or the like), amino acids, carbohydrates, lipids and modified molecules thereof.

Next, a second trapping body labeled with a fluorescent substance is bound to the substance to be detected bound to the first trapping body on the metal film 225 (secondary reaction (step S50)). Here, the second trapping body is a substance that specifically binds to a site of the substance to be detected which is different from a site to which the first trapping body specifically binds. A fluorescent substance is bound to the second trapping body. Accordingly, when the labeling solution is provided in the housing 211, the second trapping body is specifically bound to the substance to be detected which is bound to the first trapping body, and the substance to be detected is indirectly labeled with a fluorescent substance. The second trapping body may be any substance that specifically binds to a site different from the site where the first trapping body specifically binds to the substance to be detected, and may be a biomolecule specific for the substance to be detected, or may be a fragment thereof. The second trapping body may be composed of one molecule or a complex in which two or more molecules are bound to each other.

Specifically, the control unit 150 controls the pipette control unit 136 to remove the washing solution in the housing 211 and to introduce the labeling solution containing the second trapping body into the housing 211. The control unit 150 controls the vibration unit 140 to vibrate the detection chip 200 to agitate the labeling solution in the housing 211. Also at this time, from the viewpoint of appropriately proceeding the reaction, as shown in FIGS. 10A and 10B, it is preferable that the reaction field 226 is always below the vibrating liquid surface 240 of the liquid (labeling solution) in the housing 211. From the viewpoint of increasing the reaction efficiency, it is more preferable that the reaction field 226 is closer to the vibrating liquid surface 240 compared with the case of FIG. 10A, as shown in FIG. 10B. From the viewpoint of preventing the scattering of the liquid (labeling solution), it is preferable that the height of the liquid surface 240 in a state of being standing is ⅔ or less of the depth (height) of the housing 211, and more preferably ½ or less. Thereafter, the control unit 150 controls the pipette control unit 136 to remove the labeling solution in the housing 211, introduce the washing solution into the housing 211, and wash the interior of the housing 211. Also at this time, the control unit 150 controls the vibration unit 140 to vibrate the detection chip 200 to agitate the washing solution in the housing 211. The control unit 150 controls the pipette control unit 136 to remove the washing solution in the housing 211 and to introduce the measurement buffer solution into the housing 211.

Figure 10C:
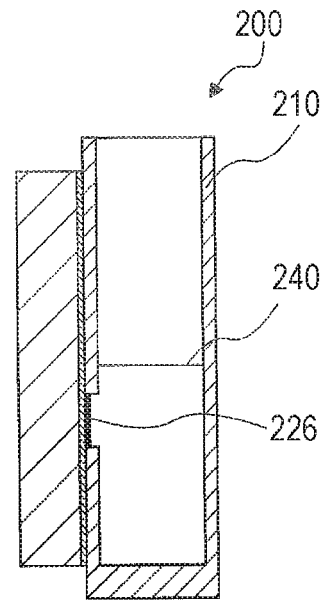
FIGS. 10C and 10D are schematic diagrams showing a relationship between a reaction field and the a liquid surface when fluorescence is detected.
Figure 10D:
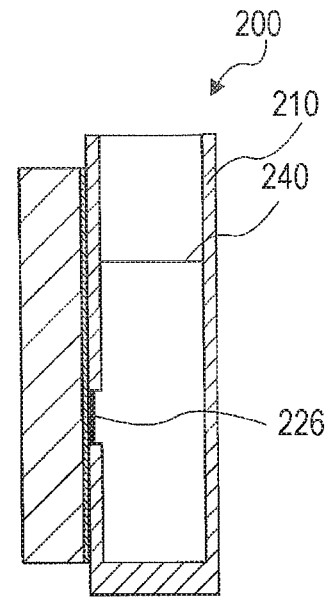

Next, the fluorescence value from the fluorescent substance labeling the substance to be detected is measured (step S60). Specifically, the control unit 150 controls the light source unit 111 to irradiate a position corresponding to the reaction field 226 of the reflection surface 223 with the excitation light α. At the same time, the control unit 150 controls the detection unit 125 to detect the light amount of light having the same wavelength as the fluorescence β. At this time, the control unit 150 controls the position switching unit 124 to move the optical filter 122 on the optical path. The control unit 150 records the measured light amount as a fluorescence value. Also at this time, from the viewpoint of appropriately detecting the fluorescence β, as shown in FIGS. 10C and 10D, it is preferable that the reaction field 226 is always below the liquid surface 240 of the liquid (measurement buffer solution) in the housing 211. On the other hand, as shown in FIG. 10C, when the reaction field 226 and the liquid surface 240 are close to each other, there is a concern that the fluorescence β reflected or refracted by the liquid surface 240 may also reach the first lens 121, and be detected by the detection unit 125. Detecting such fluorescence β influenced by the liquid surface 240 leads to a decrease in detection accuracy. Accordingly, from the viewpoint of improving the detection accuracy, it is preferable that the reaction field 226 is farther from the liquid surface 240 compared with the case of FIG. 10C, as shown in FIG. 10D. As described above, in the first step (primary reaction (step S40) and secondary reaction (step S50)) of reaction in the reaction field 226, from the viewpoint of increasing the reaction efficiency, it is preferable that the liquid surface 240 is low to some extent. On the other hand, in the second step (measurement of the fluorescence value (step S60)) of detecting light of which light amount varies according to the amount of the substance to be detected trapped in the reaction field, from the viewpoint of increasing the detection accuracy, it is preferable that the liquid surface 240 is high to some extent. In order to achieve both of them, the amount of liquid in the housing 211 in the second step (see FIG. 10D) may be larger than the amount of liquid in the housing 211 in the first step (see FIG. 10B).

Finally, the presence or amount of the substance to be detected is calculated (step S70). The fluorescence value mainly includes a fluorescent component (signal value) derived from a fluorescent substance that labels a substance to be detected, and an optical blank value. Accordingly, the control unit 150 can subtract the optical blank value obtained in step S30 from the fluorescence value obtained in step S60 to calculate a signal value correlated with the amount of the substance to be detected. Then, the control unit 150 converts the result into the amount, concentration, or the like of the substance to be detected by the calibration curve prepared in advance.

By the above procedure, the presence or amount of the substance to be detected contained in the analyte can be detected.

In the above description, the incident angle of the excitation light α is set to the enhancement angle in step S20. However, in step S20, the incident angle of the excitation light α may be set to the resonance angle. In this case, the incident angle of the excitation light α to the reflection surface 223 is scanned, and the light amount of the reflected light α' of the excitation light is detected by a reflected light detection unit that is separately installed. Then, the incident angle of the excitation light α at the time when the light amount of the reflected light α' becomes minimum is determined as the resonance angle.

(Effect)

As described above, with the detection chip 200, the detection system 100, and the detection method according to the present embodiment, in order to detect the fluorescence β without passing through the liquid surface of the liquid in the housing 211, the influence by the liquid surface and bubbles on the detection result can be suppressed and the substance to be detected can be detected with high reliability.

In addition, with the detection chip 200, the detection system 100, and the detection method according to the present embodiment, since the reaction field 226 is arranged on the side surface of the housing 211, not on the bottom surface, when the liquid in the housing 211 is removed, the pipette tip 135 is brought into contact with the bottom surface of the housing 211, so that the liquid in the housing 211 can be almost completely removed. As a result, the residual liquid amount of the analyte, the labeling solution, and the washing solution in the housing 211 is reduced, so that the reaction in the reaction unit 226 and the washing in the housing 211 that are performed subsequently can be performed efficiently. From these viewpoints, it is also possible to detect the substance to be detected with high reliability.

In the present embodiment, the detection chip, the detection system, and the detection method using the PC-SPFS have been described. However, the detection chip, the detection system, and the detection method according to the present embodiment are not limited thereto. For example, the detection chip and the detection system according to the present embodiment can also be applied to a detection method using the SPR method. In this case, the detection unit 125 detects the excitation light α' reflected by the reflection surface 223 of the prism 221, not the fluorescence β, as the light that is emitted from the detection chip 200 and the light amount of which changes depending on the amount of the substance to be detected trapped in the reaction field 226. The detection chip and the detection system according to the present embodiment can also be applied to a detection method using the evanescent fluorescence method in which a fluorescent substance that labels a substance to be detected is excited with evanescent light without using the SPR. In this case, the trapping region 227 (reaction field 226) is arranged directly on the reflection surface 223 of the prism 221 not via a metal film. When the light source unit 111 irradiates a position corresponding to the reaction field 226 on the reflection surface 223 (the inner surface of the side wall) with the excitation light α, evanescent light is generated in the reflection surface 223, and the fluorescent substance existing in the reaction field 226 due to the evanescent light is excited and emits the fluorescence β. The detection unit 125 detects the fluorescence β, as the light that is emitted from the detection chip 200 and the light amount of which changes depending on the amount of the substance to be detected trapped in the reaction field 226.

Second Embodiment

In a second embodiment, a detection chip, a detection system, and a detection method for detecting a substance to be detected by the diffraction grating coupling type SPFS (GC-SPFS) that generates SPR using a diffraction grating will be described.

Figure 11:
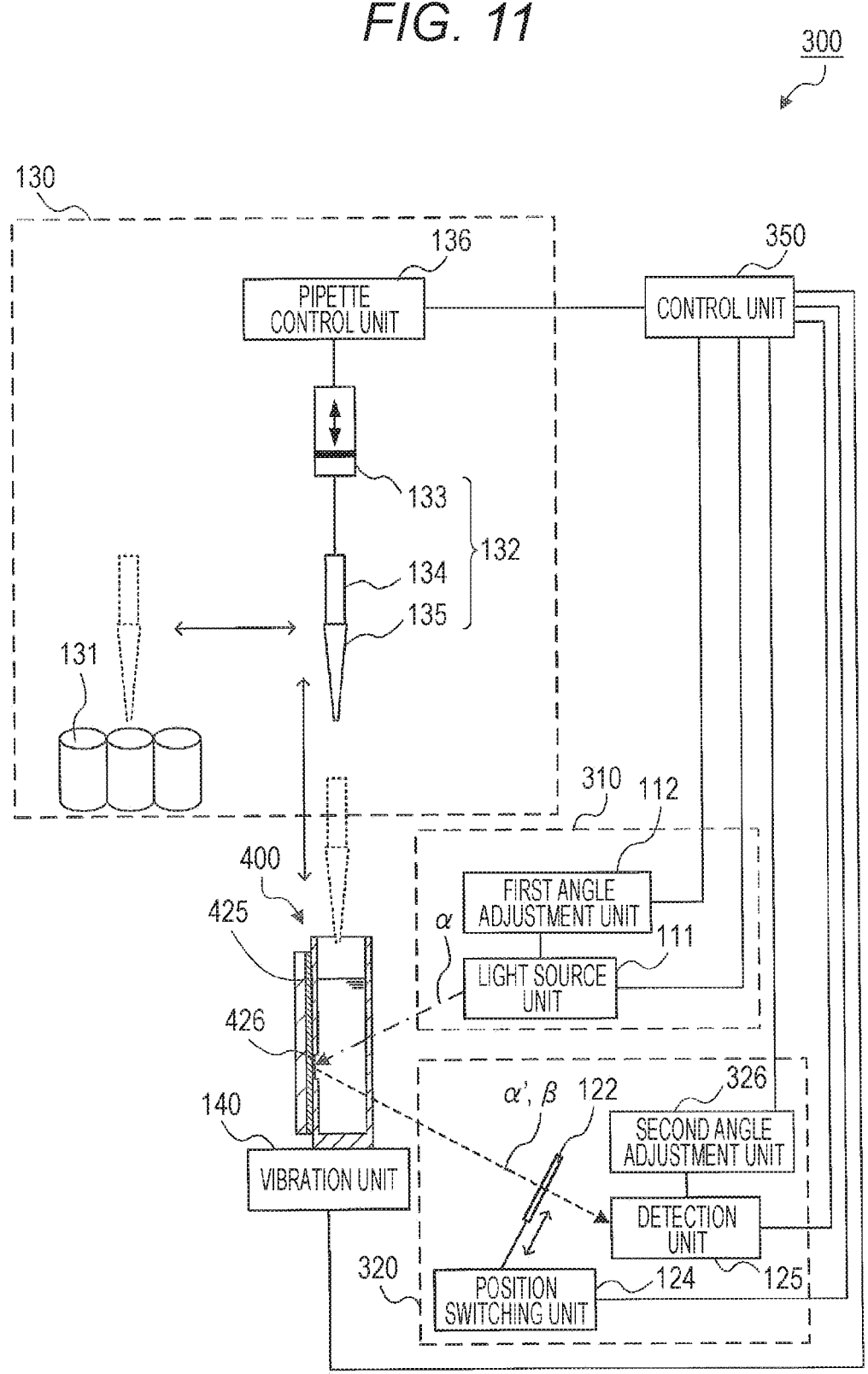
FIG. 11 is a schematic diagram showing a configuration of a detection system according to a second embodiment.

FIG. 11 is a schematic diagram showing a configuration of a detection system 300 according to the second embodiment. As shown in FIG. 11, the detection system 300 operates in a state where a detection chip 400 is mounted at a predetermined position. In addition to the detection chip 400, the detection system 300 includes an excitation light irradiation unit 310, a fluorescence detection unit 320, the liquid transfer unit 130, the vibration unit 140, and a control unit 350. In the detection system 300 according to the second embodiment, the detection chip 400 is irradiated with excitation light α such that surface plasmon resonance is generated in a diffraction grating 428 (the metal film 425) of the detection chip 400 in a state where the detection chip 400 is mounted to a predetermined position, and an enhancement electric field based on the surface plasmon resonance is generated in the vicinity of the diffraction grating 428. Then, a fluorescent substance existing in a reaction field 426 on the diffraction grating 428 is excited by the enhancement electric field, and fluorescence β emitted from the fluorescent substance is detected, so that the presence or absence and amount of a substance to be detected in the analyte is measured.

The detection system 300 according to the second embodiment is different from the detection system 100 according to the first embodiment mainly in that the detection chip 400 includes the diffraction grating 428 as an optical element, and the excitation light irradiation unit 310 irradiates the diffraction grating 428 with the excitation light α to generate the SPR. Therefore, the same reference numerals are given to the same components as those of the detection system 100 according to the first embodiment, and a description thereof will be omitted. Hereinafter, the detection chip 400 will be described first, and then the detection system 300 and its operation (detection method) will be described.

(Detection Chip)

Figure 12C:
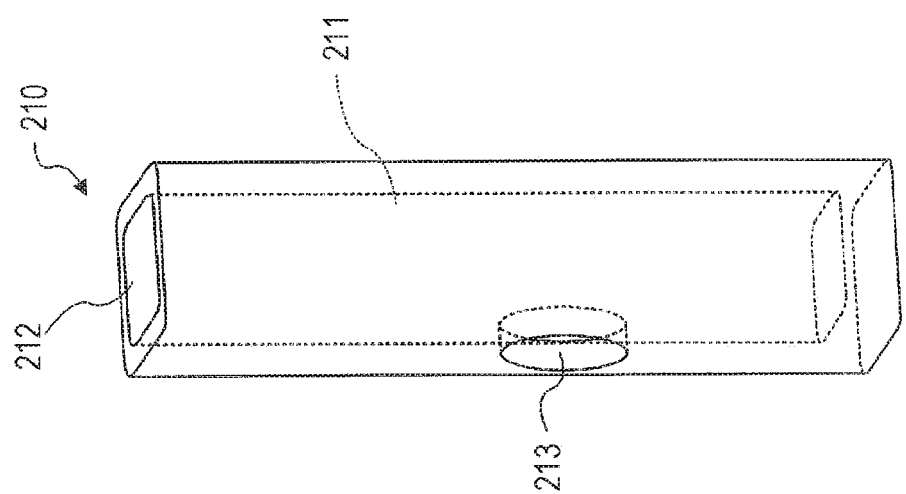
FIG. 12C is a perspective view of the well body.
Figure 12B:
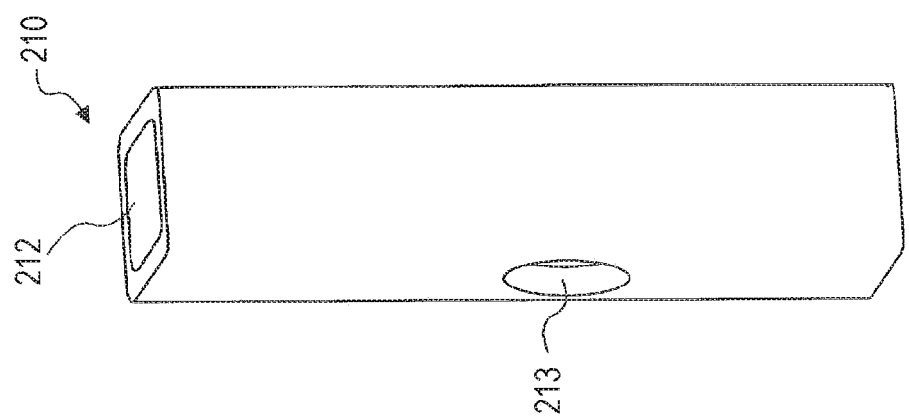
FIG. 12B is a perspective view of a well body.
Figure 12A:
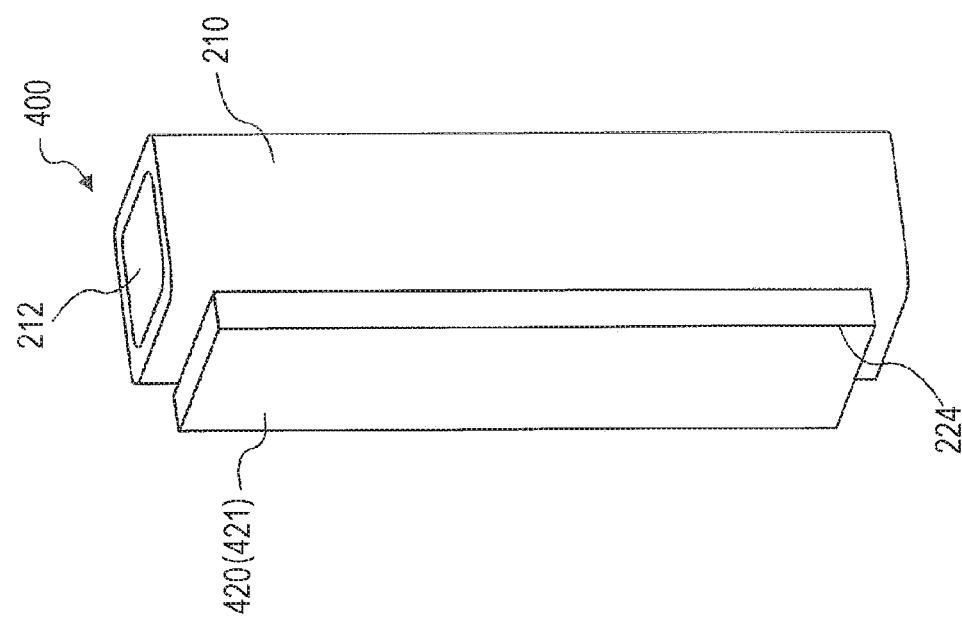
FIG. 12A is a perspective view of a detection chip according to the second embodiment.
Figure 13:
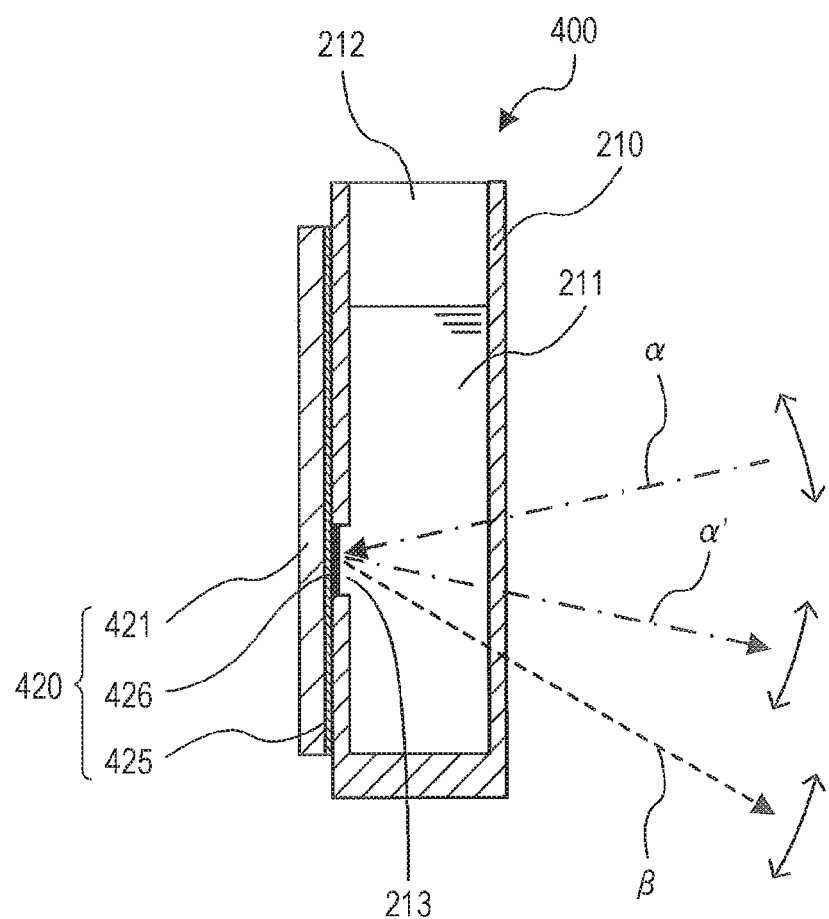
FIG. 13 is a schematic diagram showing light entering the detection chip and light emitted from the detection chip according to the second embodiment.
Figure 14:
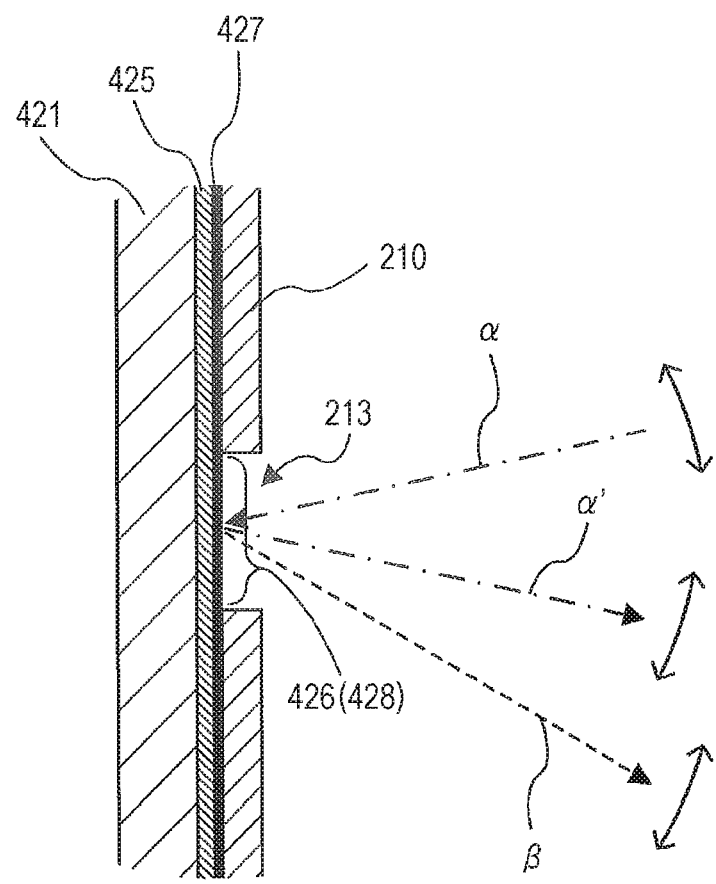
FIG. 14 is a partially enlarged cross-sectional view enlarging the vicinity of a reaction field in the cross-sectional view of FIG. 13.

FIGS. 12A to 12C are schematic diagrams showing a configuration of the detection chip 400 according to the second embodiment. FIG. 12A is a perspective view of the detection chip 400, FIG. 12B is a perspective view of a well body 210, and FIG. 12C is a perspective view of the well body 210. FIG. 13 is a schematic diagram showing light (excitation light α) entering the detection chip 400 and light (reflected light α' of excitation light and fluorescence β) emitted from the detection chip 400. FIG. 13 is a cross-sectional view taken along the height direction of the detection chip 400, and shows a state where liquid (for example, measurement buffer solution) is housed in the housing 211. FIG. 14 is a partially enlarged cross-sectional view enlarging the vicinity of the reaction field 426 in the cross-sectional view of FIG. 13.

As shown in FIGS. 12A and 13, the detection chip 400 has the well body 210 and a side wall member 420.

The well body 210 is the same as the well body 210 of the detection chip 200 according to the first embodiment. The well body 210 has a housing (well) 211 therein. The housing 211 is a bottomed recessed portion configured to be capable of housing liquid, and is opened to the outside in a first opening 212 provided in the upper portion and a second opening 213 provided in the side portion.

The well body 210 is formed of a material transparent to light (at least light having the wavelength of the excitation light α and light having the wavelength of the fluorescence β). However, a part of the well body 210 may be formed of a material opaque to light as long as the material does not hinder the light extraction in the detection method described later. At least a part of the side wall included in the housing 211 has optical transparency. In the present embodiment, at least the side wall opposed to the reaction field 426, among the four side walls included in the housing 211, has optical transparency. Examples of the material transparent to light include a resin and a glass.

In the detection chip 400 according to the present embodiment, both the light emitted from the excitation light irradiation unit 310 (excitation light α) and the light emitted from the vicinity of the reaction field 426 and detected by the detection unit 125 (the reflected light α' of the excitation light α nd the fluorescence β) pass through the side wall opposed to the reaction field 426 (see FIG. 11). Accordingly, when it is desired to suppress the refraction of these pieces of light, as shown in FIG. 13, it is preferable that both the inner surface and the outer surface of the side wall opposed to the reaction field 426 (trapping region 427) in the housing 211 are flat.

The side wall member 420 includes a substrate 421, the metal film 425, and the reaction field 426. As described above, the "reaction field" means a region in the trapping region 427 arranged on the metal film 425, the region exposed in the housing 211 via the second opening 213 (see FIG. 14). In the present embodiment, a diffraction grating 428 as an optical element is formed in at least a part of the surface of the metal film 425 corresponding to the reaction field 426. As shown in FIGS. 12A, 13, and 14, the side wall member 420 is fixed to the well body 210 such that at least a part of the trapping region 427 is exposed into the housing 211 to be the reaction field 426, and the side wall member 420 completely closes at least a part of the second opening 213.

The substrate 421 is a member for supporting the metal film 425 and closing the second opening 213 of the well body 210. The substrate 421 also functions as a side wall included in the housing 211. The shape and material of the substrate 421 are not particularly limited as long as the above function can be realized. Examples of the material of the substrate 421 include a resin and a glass. In the present embodiment, the substrate 421 is a resin plate.

The metal film 425 is arranged on the surface of the substrate 421 on the side of the well body 210. As described above, the metal film 425 is formed with the diffraction grating 428 as an optical element. The metal film 425 may be formed entirely on the surface of the substrate 421 on the side of the well body 210 or may be formed only in a part thereof. The diffraction grating 428 may be formed entirely on the surface of the metal film 425 on the side of the well body 210 or may be formed only in a part thereof. The diffraction grating 428 is formed in at least a part of a portion of the surface of the metal film 425 corresponding to the reaction field 426. When the diffraction grating 428 is irradiated with light, surface plasmon generated in the metal film 425 and evanescent light generated by the diffraction grating 428 bind to each other to generate the SPR, and an enhancement electric field localized on the surface of the metal film 425 is generated. The material of the metal film 425 is not particularly limited as long as the material is a metal capable of generating the SPR. Examples of the material of the metal film 425 include gold, silver, copper, aluminum, and alloys thereof. The method of forming the metal film 425 is not particularly limited. Examples of a method of forming the metal film 425 include sputtering, vapor deposition, and plating. The thickness of the metal film 425 is not particularly limited, but it is preferably within the range of 30 to 70 nm.

Figure 15A:
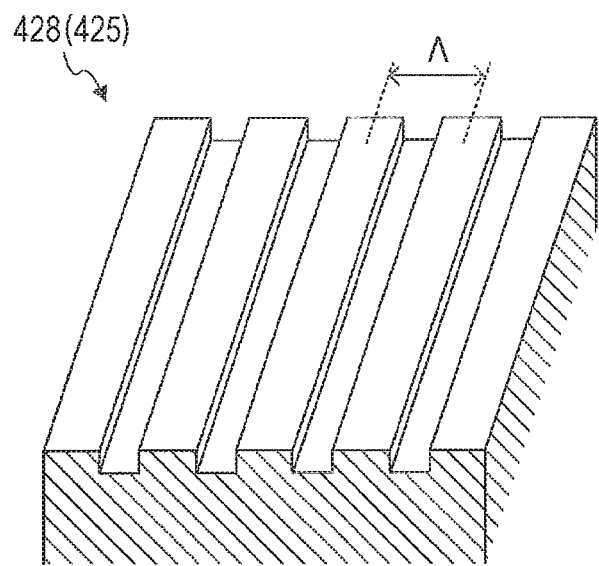
FIGS. 15A and 15B are perspective views of a diffraction grating.
Figure 15B:
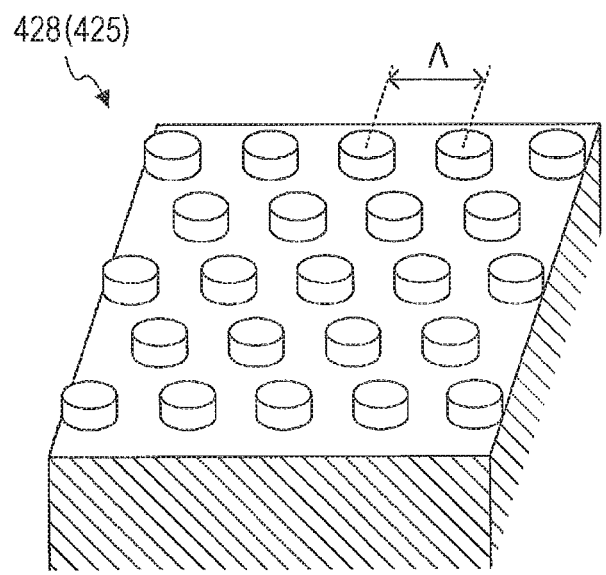

The diffraction grating 428 generates evanescent light when the metal film 425 is irradiated with light. The shape of the diffraction grating 428 is not particularly limited as long as evanescent light can be generated. For example, the diffraction grating 428 may be a one-dimensional diffraction grating as shown in FIG. 15A or a two-dimensional diffraction grating as shown in FIG. 15B. In the one-dimensional diffraction grating shown in FIG. 15A, a plurality of ridges parallel to each other are formed at predetermined intervals on the surface of the metal film 425. In the two-dimensional diffraction grating shown in FIG. 15B, protrusions having a predetermined shape are periodically arranged on the surface of the metal film 425. Examples of the array of the protrusions include a tetragonal lattice, a triangular (hexagonal) lattice, and the like. Examples of the cross sectional shape of the diffraction grating 428 include a rectangular wave shape, a sine wave shape, a saw tooth shape, and the like. The pitch of the diffraction grating is preferably in the range of 100 to 2000 nm from the viewpoint of generating the SPR. Here, the "pitch of the diffraction grating" means the center-to-center distance A between the protrusions in the array direction of the protrusions, as shown in FIGS. 15A and 15B. In the present embodiment, the diffraction grating 428 is arranged such that the array direction of the protrusions is along the depth direction of the housing 211.

The method for forming the diffraction grating 428 is not particularly limited. For example, after the metal film 425 is formed on the flat substrate 421, the metal film 425 may be provided with an uneven shape. The metal film 425 may be formed on the substrate 421 previously provided with an uneven shape. In either method, the metal film 425 including the diffraction grating 428 can be formed.

The reaction field 426 is a region for trapping the substance to be detected that is exposed in the housing 211. As described above, the reaction field 426 means a region in the trapping region 427 arranged on the metal film 425, the region exposed in the housing 211 via the second opening 213. In the present embodiment, at least a part of the reaction field 426 is located on the diffraction grating 428.

The reaction field 426 is arranged on the inner side surface of the housing 211. At this time, it is preferable that the reaction field 426 is arranged at a position away from the deepest portion of the housing 211. By adopting such a configuration, it is possible to efficiently generate a reaction in the reaction field 426 when an analyte or the like is introduced into the housing 211. It is also possible to suppress noise caused by the bottom portion of the housing 211 from being mixed in the detection result at the time of detecting the fluorescence β.

The trapping region 427 is the region in which a first trapping body for trapping a substance to be detected on the metal film 425 is immobilized. The type of the first trapping body is not particularly limited as long as the first trapping body has a recognition site for specifically binding to the substance to be detected. Examples of the first trapping body include an antibody (primary antibody) or a fragment thereof capable of specifically binding to the substance to be detected, an enzyme capable of specifically binding to the substance to be detected, and the like.

The detection chip 400 may further include the second housing 230 that can house liquid in addition to the housing 211, as similar to the first embodiment (see FIGS. 8A to 8C).

(Detection System)

Next, components other than the detection chip 400 of the detection system 300 will be described. As described above, in addition to the detection chip 400, the detection system 300 includes an excitation light irradiation unit 310, a fluorescence detection unit 320, the liquid transfer unit 130, the vibration unit 140, and a control unit 350 (see FIG. 11). The liquid transfer unit 130 and the vibration unit 140 are the same as the liquid transfer unit 130 and the vibration unit 140 of the detection system 100 according to the first embodiment.

The excitation light irradiation unit 310 irradiates the diffraction grating 428 with the excitation light α via the side wall of the well body 210 and the housing 211. In the measurement of the reflected light α' of the excitation light or the fluorescence β, the excitation light irradiation unit 310 emits only the P wave with respect to the diffraction grating 428 (the metal film 425) to the diffraction grating 428 such that the incident angle with respect to the diffraction grating 428 (the metal film 425) is the angle at which the SPR occurs in the diffraction grating 428. At this time, the excitation light irradiation unit 310 irradiates the diffraction grating 428 with the excitation light α such that the plane including the optical axis of the excitation light α and the optical axis of the reflected light α' is along the array direction of the protrusions of the diffraction grating. As described above, the "excitation light" is light that directly or indirectly excites a fluorescent substance. For example, the excitation light α is light that generates an enhancement electric field for exciting a fluorescent substance on the diffraction grating 428 when the diffraction grating 428 is irradiated with the excitation light α at the angle at which the SPR occurs in the diffraction grating 428. The excitation light irradiation unit 310 includes the light source unit 111 and the first angle adjustment unit 112. The light source unit 111 and the first angle adjustment unit 112 are the same as the light source unit 111 and the first angle adjustment unit 112 of the detection system 100 according to the first embodiment.

It is preferable that the incident angle of the excitation light α with respect to the diffraction grating 428 is set such that the intensity of the enhancement electric field formed by the SPR becomes the strongest, and as a result, the intensity of the fluorescence β from the fluorescent substance becomes the strongest. The incident angle of the excitation light α is appropriately selected according to the pitch Λ of the diffraction grating 428, the wavelength of the excitation light α, the type of metal forming the metal film 425, and the like. For example, the incident angle θ of the excitation light α is set so as to satisfy the following expression (1).

[Math. 1]

$$k_{sp} = k_0 \sin\theta + \frac{2\pi m}{\Lambda} \quad \text{Expression (1)}$$

$k_0$: wave number of excitation light $\alpha = 2\pi/(\lambda_0/n)$
$\lambda_0$: wavelength of excitation light α in vacuum
n: refractive index of medium on diffraction grating 428 (liquid in housing 211)
θ: incident angle of excitation light α with respect to diffraction grating 428
m: integer
Λ: pitch of diffraction grating 428

Here, $k_{sp}$ is the wave number of the plasmon excited at the interface between the two types of media (the interface between the metal film 425 and the liquid in the housing 211), and is defined as the following expression (2).

[Math. 2]

$$k_{sp} = \frac{\omega}{c} \cdot \sqrt{\frac{\varepsilon_1 \cdot \varepsilon_2}{\varepsilon_1 + \varepsilon_2}} \quad \text{Expression (2)}$$

ω: angular frequency of excitation light α
c: light speed
$\varepsilon_1$: dielectric constant of medium on diffraction grating 428 (liquid in housing 211)=$n^2$
$\varepsilon_2$: dielectric constant of medium (metal) forming diffraction grating 428

Since the optimal incident angle of the excitation light α varies with changes in various conditions, the first angle adjustment unit 112 adjusts the incident angle by relatively rotating the optical axis of the excitation light α and the diffraction grating 428.

The fluorescence detection unit 320 detects the fluorescence β that has been generated by irradiation of the diffraction grating 428 with the excitation light α and has passed through the housing 211 and the side wall of the well body 210. As needed, the fluorescence detection unit 320 also detects the reflected light α' of the excitation light that has been generated by irradiation of the diffraction grating 428 with the excitation light α and has passed through the housing 211 and the side wall of the well body 210. The fluorescence detection unit 320 includes the optical filter 122, the position switching unit 124, the detection unit 125, and a second angle adjustment unit 326. The optical filter 122, the position switching unit 124, and the detection unit 125 are the same as the optical filter 122, the position switching unit 124, and the detection unit 125 of the detection system 100 according to the first embodiment. Although the fluorescence detection unit 320 may further include a condenser lens to widen the detection range of the detection unit 125, it is preferable that the fluorescence detection unit 320 does not include a condenser lens from the viewpoint of reducing the background.

The second angle adjustment unit 326 relatively rotates the optical axis of the fluorescence detection unit 320 and the diffraction grating 428 to adjust the angle of the optical axis of the fluorescence detection unit 320. For example, the second angle adjustment unit 326 rotates the detection unit 125 around the intersection of the optical axis of the fluorescence detection unit 320 and the metal film 425. The second angle adjustment unit 326 appropriately adjusts the position of the detection unit 125, so that the fluorescence detection unit 320 can detect the fluorescence β at the angle at which the intensity of the fluorescence β that has emitted from the reaction field 426 (the diffraction grating 428) and has passed through the housing 211 and the side wall of the well body 210 is maximum (fluorescence peak angle). When the light source unit 111 is moved to adjust the incident angle of the excitation light α, the detection unit 125 can be moved according to the position of the light source unit 111 to detect the reflected light α'.

The control unit 350 controls the light source unit 111, the first angle adjustment unit 112, the position switching unit 124, the detection unit 125, the second angle adjustment unit 326, the pipette control unit 136, and the vibration unit 140. The control unit 350 includes, for example, a well-known computer or a microcomputer including an arithmetic device, a control device, a storage device, an input device, and an output device.

In the present embodiment, the liquid transfer unit 130 and the vibration unit 140 are arranged such that introduction and removal of liquid by the liquid transfer unit 130 and application of vibration by the vibration unit 140 can be performed on the detection chip 400 arranged at a position where the detection chip 400 can be irradiated with the excitation light α. However, the positions of the liquid transfer unit 130 and the vibration unit 140 are not limited thereto. For example, when the detection chip 400 is arranged at a first position, introduction and removal of liquid by the liquid transfer unit 130 and application of vibration by the vibration unit 140 may be performed, and when the detection chip 400 is arranged at a second position, irradiation with the excitation light α by the excitation light irradiation unit 310 and the detection of the fluorescence β by the fluorescence detection unit 320 may be performed. In this case, the detection system 300 further includes a conveyance unit for moving the detection chip 400 to the first position and the second position.

(Detection Method)

Figure 16:
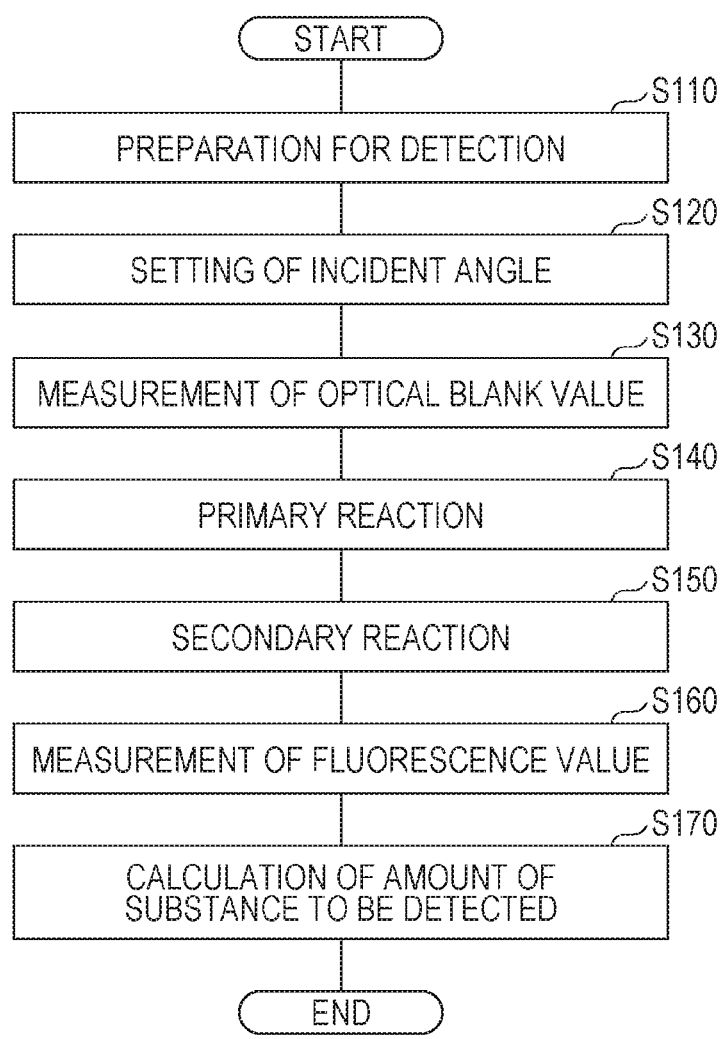
FIG. 16 is a flowchart of a detection method according to the second embodiment, and is a flowchart showing an example of an operation procedure of a detection system.

Next, a detection method of a substance to be detected using the detection system 300 will be described. FIG. 16 is a flowchart showing an example of an operation procedure of the detection system 300 at the time of performing the detection method according to the present embodiment.

First, preparation for detection is performed (step S110). Specifically, the detection chip 400 is installed at a predetermined position of the detection system 300. In the case where a humectant is present on the reaction field 426 of the detection chip 400, the interior of the housing 211 is washed so that the humectant on the reaction field 426 is removed. Thereafter, the control unit 350 controls the pipette control unit 136 to introduce the measurement buffer solution into the housing 211.

Next, the incident angle of the excitation light α to the diffraction grating 428 (the metal film 425) of the detection chip 400 is set to the resonance angle (step S120). Specifically, the control unit 350 controls the light source unit 111 and the first angle adjustment unit 112 to irradiate the diffraction grating 428 with the excitation light α, while scanning the incident angle of the excitation light α with respect to the diffraction grating 428. At the same time, the control unit 350 controls the detection unit 125 and the second angle adjustment unit 326 to detect the reflected light α' of the excitation light. At this time, the control unit 350 controls the position switching unit 124 to move the optical filter 122 out of the optical path. The control unit 350 obtains data including the relationship between the incident angle of the excitation light α and the intensity of the reflected light α'. The control unit 350 analyzes the data and determines an incidence angle (resonance angle) at which the intensity of the reflected light α' becomes minimum Finally, the control unit 350 controls the first angle adjustment unit 112 to set the incident angle of the excitation light α with respect to the diffraction grating 428 to the resonance angle.

Next, an optical blank value is measured (step S130). Specifically, the control unit 350 controls the light source unit 111 to irradiate the diffraction grating 428 with the excitation light α. At the same time, the control unit 350 controls the detection unit 125 and the second angle adjustment unit 326 to detect the light amount of background light having the same wavelength as the fluorescence β. At this time, the control unit 350 controls the position switching unit 124 to move the optical filter 122 on the optical path. In addition, the control unit 350 controls the second angle adjustment unit 326 to set the angle of the optical axis of the fluorescence detection unit 320 with respect to the perpendicular of the metal film 425 to an appropriate angle (preferably, the fluorescence peak angle in step S160). For example, the angle of the optical axis of the fluorescence detection unit 320 with respect to the perpendicular of the metal film 425 may be about twice the incident angle of the excitation light α with respect to the metal film 425. The control unit 350 records the measured light amount of the background light as a blank value.

Next, an analyte is introduced into the housing 211 of the detection chip 400, and the substance to be detected contained in the analyte is specifically bound to the first trapping body in the reaction field 426 (primary reaction (step S140)). Specifically, the control unit 350 controls the pipette control unit 136 to remove the measurement buffer solution in the housing 211 and to introduce the analyte into the housing 211. The control unit 350 controls the vibration unit 140 to vibrate the detection chip 400 to agitate the analyte in the housing 211. Thereafter, the control unit 350 controls the pipette control unit 136 to remove the analyte in the housing 211, introduce the washing solution into the housing 211, and wash the interior of the housing 211. Also at this time, the control unit 350 controls the vibration unit 140 to vibrate the detection chip 400 to agitate the washing solution in the housing 211. As similar to the detection system 100 according to the first embodiment, the types of the analyte and the substance to be detected are not particularly limited.

Next, the second trapping body labeled with a fluorescent substance is bound to the substance to be detected bound to the first trapping body on the diffraction grating 428 (secondary reaction (step S150)). As a result, the substance to be detected is indirectly labeled with the fluorescent substance. Specifically, the control unit 350 controls the pipette control unit 136 to remove the washing solution in the housing 211 and to introduce the labeling solution containing the second trapping body into the housing 211. The control unit 350 controls the vibration unit 140 to vibrate the detection chip 400 to agitate the labeling solution in the housing 211. Thereafter, the control unit 350 controls the pipette control unit 136 to remove the labeling solution in the housing 211, introduce the washing solution into the housing 211, and wash the interior of the housing 211. Also at this time, the control unit 350 controls the vibration unit 140 to vibrate the detection chip 400 to agitate the washing solution in the housing 211. The control unit 350 controls the pipette control unit 136 to remove the washing solution in the housing 211 and to introduce the measurement buffer solution into the housing 211.

Next, the fluorescence value from the fluorescent substance labeling the substance to be detected is measured (step S160). Specifically, the control unit 350 controls the light source unit 111 to irradiate the diffraction grating 428 (the reaction field 426) with the excitation light α via the side wall of the well body 210 and the measurement buffer solution in the housing 211. At the same time, the control unit 350 controls the detection unit 125 and the second angle adjustment unit 326 so that the light amount of the light having the same wavelength as the fluorescence β (most of which is fluorescence β that has passed through the measurement buffer solution in the housing 211 and the side wall of the well body 210) is detected. At this time, the control unit 350 controls the position switching unit 124 to move the optical filter 122 on the optical path. In addition, the control unit 350 controls the second angle adjustment unit 326 to set the angle of the optical axis of the fluorescence detection unit 320 with respect to the perpendicular of the metal film 425 to an appropriate angle (preferably, the fluorescence peak angle). For example, the angle of the optical axis of the fluorescence detection unit 320 with respect to the perpendicular of the metal film 425 may be about twice the incident angle of the excitation light α with respect to the metal film 425. The control unit 350 records the measured light amount as a fluorescence value.

Finally, the presence or amount of the substance to be detected is calculated (step S170). The fluorescence value mainly includes a fluorescent component (signal value) derived from a fluorescent substance that labels a substance to be detected, and an optical blank value. Accordingly, the control unit 350 can subtract the optical blank value obtained in step S130 from the fluorescence value obtained in step S160 to calculate a signal value correlated with the amount of the substance to be detected. Then, the control unit 150 converts the result into the amount, concentration, or the like of the substance to be detected by the calibration curve prepared in advance.

By the above procedure, the presence or amount of the substance to be detected contained in the analyte can be detected.

(Effect)

As described above, with the detection chip 400, the detection system 300, and the detection method according to the present embodiment, in order to detect the fluorescence β without causing the fluorescence β to pass through the liquid surface of the liquid in the housing 211, the influence by the liquid surface and bubbles on the detection result can be suppressed and the substance to be detected can be detected with high reliability.

In addition, with the detection chip 400, the detection system 300, and the detection method according to the present embodiment, since the reaction field 426 is arranged on the side surface of the housing 211, not on the bottom surface, when the liquid in the housing 211 is removed, the pipette tip 135 is brought into contact with the bottom surface of the housing 211, so that the liquid in the housing 211 can be almost completely removed. As a result, the residual liquid amount of the analyte, the labeling solution, and the washing solution in the housing 211 is reduced, so that the reaction in the reaction unit 426 or the washing in the housing 211 that is performed subsequently can be performed efficiently. From these viewpoints, it is also possible to detect the substance to be detected with high reliability.

Figure 17A:
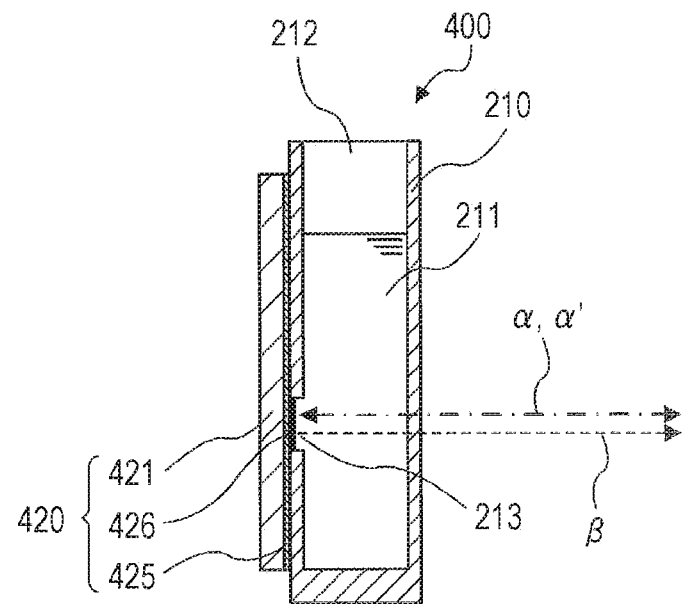
FIGS. 17A and 17B are schematic diagrams showing light entering the detection chip and light emitted from the detection chip for explaining a first modification of the detection system according to the second embodiment.
Figure 17B:
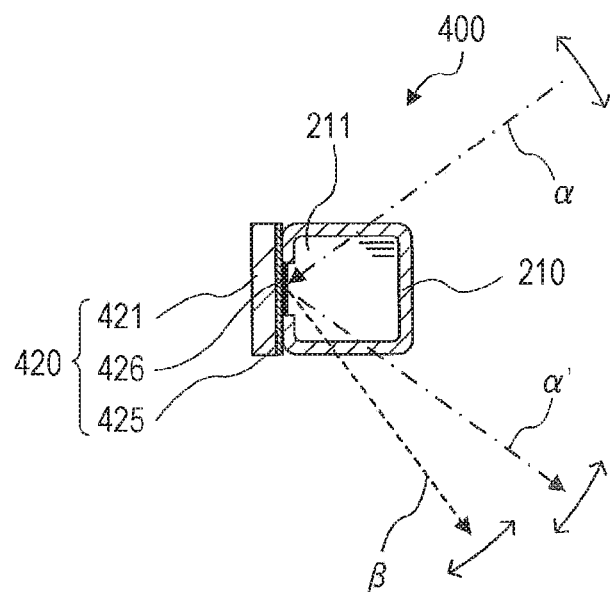

In the present embodiment, the detection chip, the detection system, and the detection method for irradiating the diffraction grating 428 with the excitation light α such that the plane including the optical axis of the excitation light α and the optical axis of the reflected light α' is along the depth direction of the housing 211, have been described. However, the detection chip, the detection system, and the detection method according to the present embodiment are not limited thereto. For example, as shown in FIGS. 17A and 17B, in the detection system according to the present embodiment, irradiation may be performed with respect to the diffraction grating 428 with the excitation light α such that the plane including the optical axis of the excitation light α and the optical axis of the reflected light α' is along the horizontal direction. In this case, the diffraction grating 428 is arranged such that the array direction of the protrusions is along the horizontal direction, and the fluorescence β may also be emitted along the horizontal direction. Accordingly, the light source unit 111 and the detection unit 125 may be arranged at the same height as the detection chip 400. In this case, depending on the shape of the housing 211, it is also possible to perform irradiation with the excitation light α through one of two side walls other than the side wall on the side where the reaction field 426 is arranged and the side wall opposed to the reaction field 426 among the four side walls included in the housing 211, and perform irradiation with the excitation light α through another of the two side walls to detect the fluorescence β. Of course, depending on the shape of the housing 211, it is also possible perform irradiation with the excitation light α through the side wall opposed to the reaction field 426 among the four side walls included in the housing 211 to detect the fluorescence β.

Figure 18A:
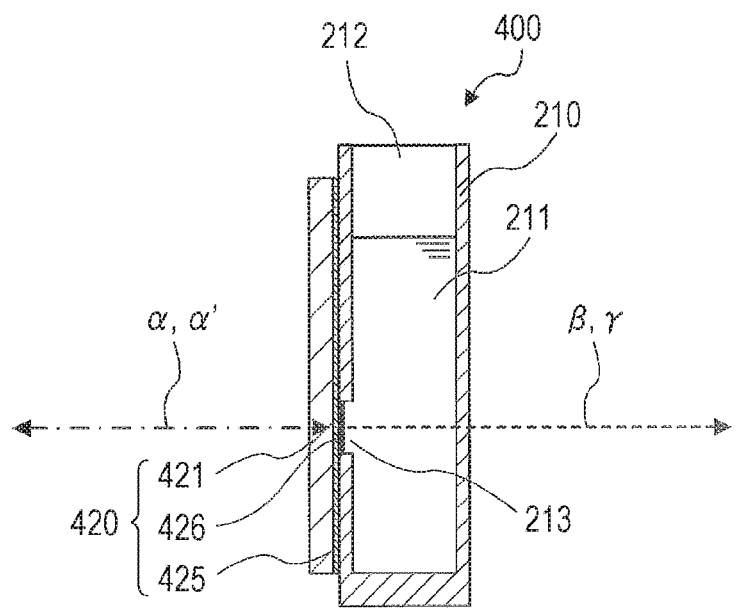
FIGS. 18A and 18B are schematic diagrams showing light entering the detection chip and light emitted from the detection chip for explaining a second modification of the detection system according to the second embodiment.
Figure 18B:
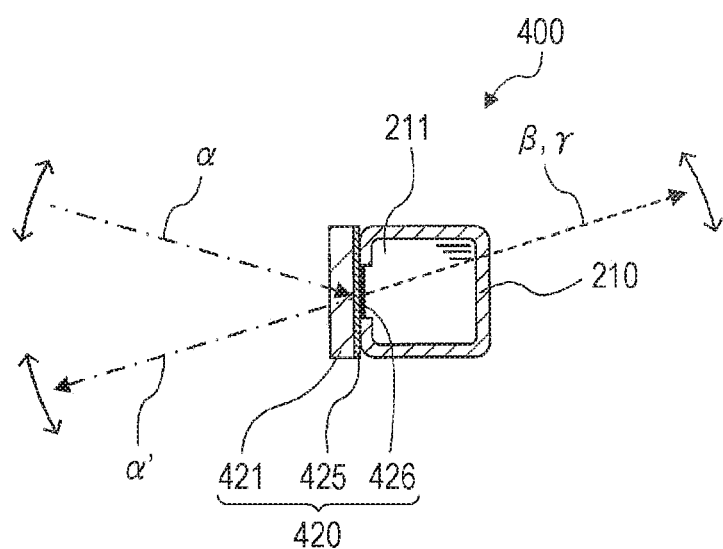
Figure 19:
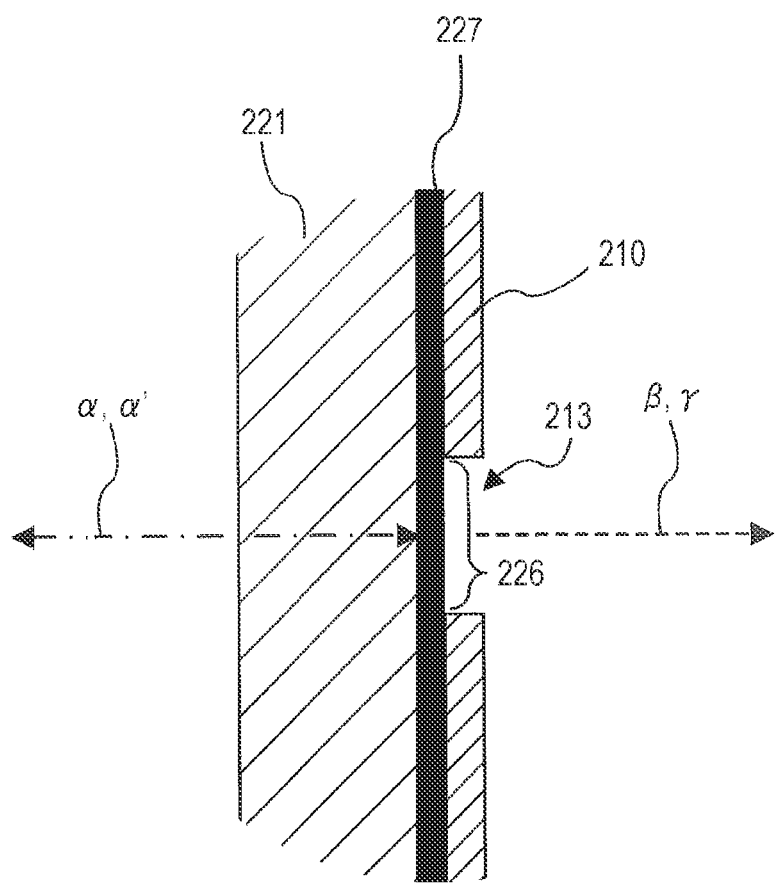
FIG. 19 is a partially enlarged cross-sectional view enlarging the vicinity of a reaction field in the cross-sectional view of the detection chip where the trapping region (reaction field) is arranged directly on the reflection surface of the prism not via a metal film.

In the present embodiment, the detection chip, the detection system, and the detection method for irradiating the diffraction grating 428 with the excitation light α from the housing 211 side have been described. However, the detection chip, the detection system, and the detection method according to the present embodiment are not limited thereto. For example, as shown in FIGS. 18A and 18B, in the detection system according to the present embodiment, irradiation may be performed with respect to the diffraction grating 428 with the excitation light α from the substrate 421 side (see, for example, the following Non Patent Literature 1). When the diffraction grating 428 is irradiated with the excitation light α from the substrate 421 side as described above, part of the excitation light α passes through the metal film 425 and reaches the diffraction grating 428 to generate the SPR. Then, the fluorescent substance is excited by the electric field enhanced by the SPR, and fluorescence β having directivity in a predetermined direction is emitted. Accordingly, the light source unit 111 and the detection unit 125 may be arranged at the same height as the detection chip 400. The detection chip 400 is located between the light source unit 111 and the detection unit 125 (see FIG. 1). Note that, in the example shown in FIGS. 18A and 18B, the diffraction grating 428 is arranged such that the array direction of the protrusions is along the horizontal direction, and the fluorescence β may also be emitted along the horizontal direction. In the case of irradiating the diffraction grating 428 with the excitation light α from the substrate 421 side as described above, it is preferable that the substrate 421 is formed of a dielectric transparent to the excitation light α, and the diffraction grating 428 is formed on both surfaces of the metal film 425. Examples of the material of the substrate 421 include a resin and a glass that are transparent to the excitation light α. For example, a diffraction grating 428 can be formed on both surfaces of the metal film 425 by forming a diffraction grating by nanoimprinting using a UV resin on the surface of the substrate 421 formed of a resin, and forming the metal film 425 thereon. In the case of irradiating the diffraction grating 428 with the excitation light α from the substrate 421 side as described above, the incident angle of the excitation light α may be set to the resonance angle in step S20, but the incident angle of the excitation light α may be set to the enhancement angle. When the incident angle of the excitation light α is set to the enhancement angle, the incidence angle of the excitation light α to the metal film 425 is scanned and the light amount of the plasmon scattered light γ emitted from the diffraction grating 428 is detected by the detection unit 125. Then, the incident angle of the excitation light α at the time when the light amount of the plasmon scattered light γ becomes maximum is determined as the enhancement angle.

Non Patent Literature 1: Tawa K., et al., "Zinc Oxide-Coated Plasmonic Chip Modified with a Bispecific Antibody for Sensitive Detection of a Fluorescent Labeled-Antigen", Anal. Chem., Vol. 83, pp. 5944-5948.

Other Embodiments

In each of the embodiments described above, the embodiments of using the detection chip 200 in which the side wall member 220 includes the prism 221 as the optical element or the detection chip 400 in which the side wall member 220 includes the diffraction grating 428 as the optical element have been described. However, the detection chip may include other optical elements. Examples of the optical element that the detection chip may include a member (for example, a diffraction grating, a nanohole array, a nanoparticle layer, or the like) in which a prism, a minute protrusion or a recess is periodically arrayed, an optical waveguide (including an optical fiber), and a light reflection member. Regardless of the type of optical element, the reaction field is arranged on the optical element, directly or via another member (for example, a metal film).

As described in the first embodiment, when the side wall member includes a prism, the substance to be detected can be detected using the PC-SPFS, the SPR method, the evanescent fluorescence method, or the like. In this case, the reaction field is arranged on the reflection surface of the prism via a metal film or not via a metal film.

As described in the second embodiment, in the case where the side wall member includes a diffraction grating in which minute protrusions or recesses are periodically arrayed and the surface of the diffraction grating is covered with a metal, the GC-SPFS or the like can be used to detect the substance to be detected. In this case, the reaction field is arranged on the diffraction grating.

On the other hand, when the side wall member includes a nanohole array in which nano-sized through holes are provided at predetermined intervals in the metal film, the substance to be detected can be detected using a detection method using the SPR or the like (see, for example, the following Non Patent Literature 2). In this case, the nanohole array is exposed in the housing via the second opening, and the reaction field is arranged on the nanohole array.

Non Patent Literature 2: De Leebeeck A., et al., "On-Chip Surface-Based Detection with Nanohole Arrays", Anal. Chem., Vol. 79, pp. 4094-4100.

When the side wall member includes a nanoparticle layer in which nanoparticles covered with a metal are arrayed, the substance to be detected can be detected using a detection method using the localized surface plasmon resonance (LSPR) or the like (see, for example, the following Non Patent Literature 3). In this case, the nanoparticle layer is exposed in the housing via the second opening, and the reaction field is arranged on the nanoparticle layer.

Non Patent Literature 3: Kurita M, "Precious Metals for Localized Surface Plasmon Resonance Measurement Applications", J. Surf. Finish. Soc. Jpn., Vol. 62, pp. 306-308.

When the side wall member includes an optical fiber, the substance to be detected can be detected using a detection method using the SPR, a detection method using the evanescent light, or the like (see, for example, the following Non Patent Literatures 4 and 5). In this case, at least a part of the side surface of the optical fiber is exposed into the housing via the second opening, and the reaction field is arranged on the side surface of the optical fiber exposed into the housing via the metal film.

Non Patent Literature 4: Slavik R., et al., "A miniature fiber optic surface plasmon resonance sensor for fast detection of staphylococcal enterotoxin B", Biosensors and Bioelectronics, Vol. 17, pp. 591-595.

Non Patent Literature 5: Tsunoda K., "Waveguide Chemical- and Bio-Sensors Using Evanescent Wave", Kogaku (Japanese Journal of Optics: Publication of the Optical Society of Japan), Vol. 34, pp. 513-517.

When the side wall member includes an optical waveguide, the substance to be detected can be detected using a detection method using the evanescent light, or the like (see, for example, the following Non Patent Literature). In this case, at least a part of the side surface of the optical waveguide is exposed into the housing via the second opening, and the reaction field is arranged on the side surface of the optical waveguide exposed into the housing.

Non Patent Literature 6: Higashino I., "Simple Quantitative Test Technique for Small Clinical Tester Using Optical Waveguide Sensor", Toshiba Review, Vol. 67, pp. 60-61.

When the side wall member includes a light reflection member, the substance to be detected can be detected using a detection method using the reflection interference spectroscopy (RIfS), or the like (see, for example, the following Non Patent Literature 7). In this case, the light reflection member is exposed in the housing via the second opening, and the reaction field is arranged on the light reflection member.

Non Patent Literature 7: Kurihara Y. et al., "The Promise of Expanding Areas of Application for Reflectometric Interference Spectroscopy", Konica Minolta Technology Report, Vol. 9, pp. 29-35.

This application claims priority based on Japanese Patent Application 2016-148345 filed on Jul. 28, 2016. The contents described in the application specification and drawings are all incorporated herein by reference.

INDUSTRIAL APPLICABILITY

With the detection chip, the detection system, and the detection method according to the present invention, it is possible to prevent deterioration of detection accuracy due to remaining liquid in a housing during a reaction process, and reduce influence by a liquid surface of the liquid in the housing during a detection process to detect the substance to be detected with high reliability. Accordingly, the detection chip, the detection system, and the detection method according to the present invention are useful for, for example, a clinical test or the like.

REFERENCE SIGNS LIST 100, 300 Detection system
110, 310 Excitation light irradiation unit
111 Light source unit
112 First angle adjustment unit
120, 320 Fluorescence detection unit
121 First lens
122 Optical filter
123 Second lens
124 Position switching unit
125 Detection unit
130 Liquid transfer unit
131 Liquid chip
132 Pipette
133 Syringe pump
134 Nozzle unit
135 Pipette tip
136 Pipette control unit
140 Vibration unit
150, 350 Control unit
200, 400 Detection chip
210 Well body
211 Housing
212 First opening
213 Second opening
214 Holding unit
220, 420 Side wall member
221 Prism
222 Entrance surface
223 Reflection surface
224 Exit surface
225, 425 Metal film
226, 426 Reaction field
227, 427 Trapping region
230 Second housing
240 Liquid surface
326 Second angle adjustment unit
421 Substrate
428 Diffraction grating
α Excitation light
α' Reflected light of excitation light
β Fluorescence
γ Plasmon scattered light

The invention claimed is:

1. A detection chip comprising:
a well body including a housing having an opening hole at an upper portion and an opening hole at a side portion; and
a side wall member on which a trapping region for trapping a substance to be detected is arranged, wherein at least a part of the trapping region of the side wall member is exposed into the housing via the opening hole in the side portion of the housing, and the side wall member is fixed to the well body so as to cover at least a part of the opening hole in the side portion of the housing.

2. The detection chip according to claim 1, wherein the side wall member includes an optical element.

3. The detection chip according to claim 2, wherein the optical element is one of: a prism, a component in which protrusions or recesses are periodically arrayed, an optical waveguide, or a light reflection member.

4. The detection chip according to claim 3, wherein
the optical element is the prism, the prism includes an entrance surface for allowing light to enter and a reflection surface for reflecting light that has entered the entrance surface,
the reflection surface of the prism is configured for generating evanescent light or configured for generating plasmon scattered light via a metal film, and
the trapping region is arranged on the reflection surface not via the metal film or via the metal film.

5. The detection chip according to claim 4, wherein
the side wall member has the metal film arranged on the reflection surface, and
the trapping region is arranged on the metal film.

6. The detection chip according to claim 3, wherein
the optical element is a diffraction grating in which the protrusions or the recesses are periodically arrayed and whose surface is covered with a metal,
the diffraction grating is exposed into the housing via the opening hole in the side portion of the housing,
the trapping region is arranged on the diffraction grating, and
at least a part of a side wall included in the housing of the well body has optical transparency.

7. The detection chip according to claim 2, wherein a side wall of the well body opposed to the trapping region, among side walls included in the housing, has optical transparency.

8. The detection chip according to claim 2, wherein the opening hole in the side portion of the housing is apart from a bottom of the housing.

9. The detection chip according to claim 2, further comprising a holder that protrudes laterally from the well body or the side wall member.

10. The detection chip according to claim 1, wherein a side wall of the well body opposed to the trapping region, among side walls included in the housing, has optical transparency.

11. The detection chip according to claim 1, wherein the opening hole in the side portion of the housing is apart from a bottom of the housing.

12. The detection chip according to claim 1, further comprising a holder that protrudes laterally from the well body or the side wall member.

13. A detection system comprising:
a detection chip including:
a well body including a housing having an opening hole at an upper portion and an opening hole at a side portion, and
a side wall member comprising a diffraction grating or a prism including an entrance surface for allowing light to enter and a reflection surface for reflecting light that has entered the entrance surface, wherein the side wall member is configured for generating evanescent light or configured for generating plasmon scattered light via a metal film, a reaction field for trapping a substance to be detected is arranged on the side wall member not via the metal film or via the metal film, and the reaction field of the side wall member is exposed into the housing via the opening hole in the side portion of the housing;
a light source that irradiates the detection chip with light from the outside such that the evanescent light is generated on the side wall member at a position corresponding to the reaction field or surface plasmon resonance is generated in the metal film; and
a detector that, when the light source irradiates the detection chip with light, detects light that is emitted from the detection chip and the light amount of which changes depending on the amount of the substance to be detected that has been trapped in the reaction field.

14. The detection system according to claim 13, wherein
the detection chip includes the metal film arranged on the side wall member,
the reaction field is arranged on the metal film,
the side wall member on which the metal film is arranged has optical transparency, and a side wall of the well body opposed to the reaction field, among side walls included in the housing, has optical transparency,
the light source irradiates the side wall member on which the metal film is arranged with light such that plasmon resonance is generated in the metal film, and
when the light source irradiates the side wall member on which the metal film is arranged with light, the detector detects fluorescence that has been emitted from a fluorescent substance labeling a substance to be detected trapped in the reaction field and has passed through the side wall of the well body opposed to the reaction field.

15. The detection system according to claim 13, wherein
the detection chip includes the metal film arranged on the side wall member, and formed with the diffraction grating on a surface of the metal film,
the reaction field is arranged on the diffraction grating,
at least a part of side walls included in the housing of the detection chip has optical transparency,
the light source irradiates the diffraction grating with light such that plasmon resonance is generated in the metal film, and
when the light source irradiates the diffraction grating with light, the detector detects fluorescence that has been emitted from a fluorescent substance labeling a substance to be detected trapped in the reaction field and has passed through the part of the side walls having the optical transparency.

16. The detection system according to claim 13, further comprising a vibrator that vibrates the detection chip for agitating liquid housed in the housing.

17. A detection method comprising:
causing a substance to be detected to be trapped in a reaction field of a detection chip comprising a well body including a housing having an opening hole at an upper portion and an opening hole at a side portion, wherein the detection chip further comprises a side wall member containing a diffraction grating or a prism, the prism includes an entrance surface for allowing light to enter and a reflection surface for reflecting light that has entered the entrance surface, the side wall member is configured for generating evanescent light or configured for generating plasmon scattered light via a metal film, the reaction field is arranged on the side wall member not via the metal film or via the metal film, and the reaction field of the side wall member is exposed into the housing via the opening hole in the side portion of the housing; and irradiating the detection chip with light from the outside such that the evanescent light is generated on the side wall member at a position corresponding to the reaction field or surface plasmon resonance is generated in the metal film, and detecting light that is emitted from the detection chip and the light amount of which changes depending on the amount of the substance to be detected that has been trapped in the reaction field.

18. The detection method according to claim 17, wherein the detection chip includes the metal film arranged on the side wall member, the reaction field is arranged on the metal film, the side wall member on which the metal film is arranged has optical transparency, and a side wall of the well body opposed to the reaction field, among side walls included in the housing, has optical transparency, in the causing a substance to be detected to be trapped, the substance to be detected is trapped in the reaction field of the detection chip, and the substance to be detected that has been trapped in the reaction field is labeled by a fluorescent substance, in the irradiating the detection chip with the light and detecting the light, the side wall member on which the metal film is arranged is irradiated with the light such that plasmon resonance is generated in the metal film, and fluorescence that has been emitted from the fluorescent substance labeling the substance to be detected trapped in the reaction field and has passed through the side wall of the well body opposed to the reaction field is detected.

19. The detection method according to claim 17, wherein the detection chip includes the metal film arranged on the side wall member and formed with the diffraction grating on a surface of the metal film, the reaction field is arranged on the diffraction grating, at least a part of side walls included in the housing of the detection chip has optical transparency, in the causing the substance to be detected to be trapped, the substance to be detected is trapped in the reaction field of the detection chip, and the substance to be detected that has been trapped in the reaction field is labeled by a fluorescent substance, in the irradiating the detection chip with the light and detecting the light, the diffraction grating is irradiated with the light such that plasmon resonance is generated in the metal film, and fluorescence that has been emitted from the fluorescent substance labeling the substance to be detected trapped in the reaction field and has passed through the the part of the side walls having the optical transparency is detected.

20. The detection method according to claim 17, wherein, in the causing the substance to be detected to be trapped, the detection chip is vibrated in a state where liquid is housed in the housing.

* * * * *